United States Patent [19]
Kasahara et al.

[11] Patent Number: 5,548,354
[45] Date of Patent: Aug. 20, 1996

[54] METHOD FOR OBSERVING AND PHOTOGRAPHING A CORNEA AND APPARATUS FOR THE SAME

[75] Inventors: Tatsuya Kasahara; Hamada Yoichi, both of Nishinomiya, Japan

[73] Assignee: Konan Common Co., Ltd., Hyogo, Japan

[21] Appl. No.: 257,374

[22] Filed: Jun. 9, 1994

[30] Foreign Application Priority Data

Jun. 10, 1993 [JP] Japan .................................. 5-166132
Jul. 15, 1993 [JP] Japan .................................. 5-198951
Oct. 29, 1993 [JP] Japan .................................. 5-294177

[51] Int. Cl.$^6$ .............................. A61B 3/14; A61B 3/10; G03B 29/00
[52] U.S. Cl. .......................... 351/206; 351/208; 351/210; 351/246; 354/62
[58] Field of Search ..................... 351/205, 206, 351/208, 210, 211, 214, 221, 246; 354/62; 128/648

[56] References Cited

U.S. PATENT DOCUMENTS 5,107,851  4/1992  Yano et al. .............................. 128/648
5,381,194  1/1995  Nishio et al. ........................... 351/208

Primary Examiner—William L. Sikes
Assistant Examiner—Huy Mai
Attorney, Agent, or Firm—Koda and Androlia

[57] ABSTRACT

An apparatus for observing and photographing cornea cells including an indicator projecting means, and eye-front observation optical system, an illuminating system for illuminating through a slit the eyeball surface obliquely, an enlarged imaging optical system for forming an enlarged image of the subject part by a TV camera based on the illuminating light, and a cornea self-focusing detector which is automatically moved in X and Y directions with respect to the optical axis of the eye-front observation optical system such that the light spot on the monitor screen by the reflected light from the subject part of the position detection indicator is brought to a specified position on the screen whereby an enlarged image of the cells is recorded and photographed and displayed simultaneously with the eye-front image in which the light spot of the photographing sight is positioned.

19 Claims, 8 Drawing Sheets

METHOD FOR OBSERVING AND PHOTOGRAPHING A CORNEA AND APPARATUS FOR THE SAME

BACKGROUND OF THE INVENTION

1. Field of the Invention

The present invention relates to methods and apparatus for obtaining images of a cornea, by which enlarged images of cornea cells such as cornea endothelium cells or cornea epithelium cells of an eyeball of a subject can be observed or photographed.

2. Description of the Prior Art

For seeing influences of contact lenses or for medical examination and treatment before and after an operation of cataract, it is necessary to observe the state of cornea endothelium cells. Therefore, for observation or photographing of cornea endothelium cells of an eyeball of a subject with their enlarged images, there have conventionally been used apparatus in which with an objective lens of a microscope of non-contact type or contact type with respect to the eyeball surface of the subject, slit illuminating light is applied toward an observation part obliquely of the eye axis and separated into reflected light from the cornea surface and image rays of light of endothelium cells so that an image of the cornea endothelium cells of the subject part are imaged by a TV camera or the like. Meanwhile, there has been proposed an ophthalmological apparatus equipped with a so-called alignment device for aligning the imaging center axis of the apparatus with the eye axis to make the TV camera focused on the subject part, such as disclosed in Japanese Patent Laid-Open Publication No. HEI 2-283352.

In these conventional apparatus, the focusing on the cornea endothelium has been accomplished in the following way. That is, the eye axis of the subject is aligned with the optical axis of the microscope (optical-axis adjustment) by manually moving a microscope frame, on which a TV camera is mounted, up and down or right and left with the use of an operation member such as a joy stick so that the alignment indicator light is located at the center of the pupil of the eye on a monitor screen. In this state, the frame, which is the main body, is moved back and forth also manually, so that the focusing is accomplished. As a result, substantial labors and skills have been required for the focusing on the cornea endothelium cells of the subject part. Further, in making observation or photographing with the above apparatus, there have been demands for observing or photographing not only the center part but also various sites of the cornea with their enlarged images, depending on what is examined in the medical treatment. However, only enlarged images of observation or photographing could hardly make it known which site of the cornea is shown.

Furthermore, these apparatus, although capable of observing or photographing the cornea endothelium, have been incapable of observing or photographing the cornea epithelium cells with their enlarged images, to a disadvantage.

In doing this, even if it is attempted that the slit illuminating light is applied toward the observation subject part obliquely of the eye axis so that the cornea epithelium cells of the subject part are imaged by a TV camera or the like with the reflected light from the cornea epithelium cells, reflected light from the cornea epithelium surface normally overlaps with reflected light from the lachrymal layer (including the mucin layer) that makes the epithelium surface normally wet, making it impossible to photograph enlarged images of the cornea epithelium cells. Still more, recently, there has been a desire for obtaining enlarged images of the cornea epithelium cells for use of examining aches of the cornea due to normal use of contact lenses.

SUMMARY OF THE INVENTION

The present invention has been achieved in view of the above problems. Accordingly, a principal, basic object of the present invention is to provide a method and an apparatus for obtaining images of a cornea, which do not require labors or skills of the operator and which allow cornea endothelium cells of a subject part to be automatically observed or photographed with their enlarged images only by activating the apparatus in a state that the head of a subject has been fixed on a jaw plate and thereafter the subject has been made fixedly viewing a fixed view marker by the subject eye. Another object of the invention is to provide an apparatus which allows the position of an enlarged part for observation or photographing to be known simultaneously when the observation is exercised or when an enlarged-photograph record is viewed later, and which allows the thickness of cornea of a subject eye to be measured simultaneously when the observation or photographing with an enlarged image is exercised. Yet another object of the invention is to provide an apparatus for obtaining images of a cornea which is capable of photographing enlarged images of cornea epithelium.

To achieve the above objects, in the method for obtaining images of a cornea according to the present invention, indicator light for alignment is projected toward a subject eye coaxially with the optical axis of an eye-front observation optical system, and reflected light from the cornea is imaged by a TV camera. Then, in correspondence to the position of the reflected light on a monitor screen, a whole imaging system which comprises an eye-front observation optical system, an illuminating system which is formed integrally with the eye-front observation optical system and which illuminates through a slit an eyeball surface in a direction different from that in which the observation optical system does, and an enlarged-imaging optical system capable of observing or photographing a subject part with its enlarged image by a TV camera based on the slit illuminating light with which the eyeball surface has been illuminated is moved automatically in a direction perpendicular to the optical axis of the observation optical system, so that the light spot on the monitor screen by the reflected light is brought to a specified position such as the center of the screen. When the light spot has entered a preset Specified area of the screen in this way, the whole imaging system is started to move forward so as to track the light spot in a direction for the eye examination by narrowing the range of detection of the light spot. During this forward movement, the focusing of the enlarged-imaging optical system on the subject part of cornea is detected by a photo-detector having a light-receiving surface at such a position that its optical path is other than that of the TV camera on the optical axis of the enlarged-imaging optical system. Thus, an enlarged image of the cornea cells of the subject part is obtained.

Also, in another method for obtaining images of a cornea according to the present invention, indicator light for alignment is projected toward a subject eye coaxially with the optical axis of an eye-front observation optical system, and reflected light from the cornea is imaged by a TV camera. Then, in correspondence to the position of the reflected light on a monitor screen, a whole imaging system which comprises an eye-front observation optical system, an illuminating system which illuminates through a slit an eyeball surface in a direction different from that in which the observation optical system does, and an enlarged-imaging optical system capable of observing or photographing a subject part with its enlarged image by a TV camera based on the slit illuminating light is moved automatically in a direction perpendicular to the optical axis of the observation optical system, so that the light spot on the monitor screen by the reflected light is brought to a specified position such as the center of the screen. When the light spot has entered a preset specified area of the screen in this way, the whole imaging system is started to move forward so as to track the light spot in a direction for the eye examination. During this forward movement, the focusing of the enlarged-imaging optical system on the subject part of cornea is detected by a photo-detector having a light-receiving surface at such a position that its optical path is other than that of the TV camera on the optical axis of the enlarged-imaging optical system. Thus, an enlarged image of the cornea cells of the subject part is obtained. In addition to this, after the enlarged image of the cornea cells of the subject part has been obtained by the imaging system, the imaging system is moved in the direction perpendicular to the optical axis of the observation optical system in such a way that its travel in the Y-direction remains the same and that its travel in the X-direction is canceled. Moreover, the imaging system is made to automatically return toward the initial setting side by a specified small extent with respect to the position at which the focusing of the cornea cells has been detected, where the imaging system stands by.

The subject part, whichever cornea endothelium or cornea epithelium, may be tracked by the above method to detect the focusing, so that an enlarged image of the cornea cells of the subject part is obtained.

On the other hand, an apparatus for obtaining images of a cornea according to the present invention comprises at least: an illuminating system for illuminating through a slit an eyeball surface of a subject eye; an enlarged-imaging optical system for forming an enlarged image of the subject part based on the slit illuminating light with which the eyeball surface has been illuminated; a focusing-detection use photo-detector arranged so as to detect a position where the enlarged-imaging optical system has been focused on the subject part via an optical path other than that in which the enlarged-imaging optical system has been focused on the imaging surface of the enlarged image; means for moving the whole imaging system, which comprises the illuminating system, the enlarged-imaging optical system, and the focusing-detection use photo-detector, in a direction for the eye examination to bring the whole imaging system to the focusing position of the subject part, by a signal derived from focusing-detection use photo-detector; and means for generating an imaging signal based on the signal representing that the focusing of the subject part has been detected by the focusing-detection use photo-detector, whereby an enlarged image of cornea cells of the subject part can be obtained.

More advantageously, another apparatus for obtaining images of a cornea according to the present invention comprises: position-detection indicator projecting means disposed opposite to a subject eye; eye-front observing means equipped with an eye-front observation optical system; an illuminating system for illuminating through a slit an eyeball surface of the subject eye; enlarged-observation means equipped with an enlarged-imaging optical system for imaging and observing an enlarged image of the subject part based on illuminating light with which the eyeball surface has been illuminated; subject-part focusing detection means for detecting by a focusing-detection use photo-detector that the enlarged-imaging optical system has been focused on the subject part; means for moving the whole imaging system, which comprises the position-detection indicator projecting means, the eye-front observation optical system, the illuminating system, the enlarged-imaging optical system, and the focusing-detection use photo-detector, in both a direction perpendicular to the optical axis of the observation optical system and a direction for the eye examination, with respect to the subject eye; and means for recording both an eye-front image in the eye-front observation means and an enlarged image of the subject part in the enlarged-observation means, wherein reflected light of the position-detection indicator derived from the subject part is brought to a specified position of the eye-front image in the eye-front observation means and thereafter the eye-front image is recorded, and wherein an enlarged image of the cornea cells of the subject part is recorded by a focusing detection signal derived from the subject-part focusing detection means.

More effectively, the focusing-detection use photo-detector is a photo-detector arranged so as to detect both a cornea-epithelium focusing position and a cornea-endothelium focusing position by the enlarged-imaging optical system, while the cornea imaging system comprises means for detecting a travel of the imaging system from the cornea-epithelium focusing position to the cornea-endothelium focusing position, the positions having been detected by the focusing-detection use photo-detector, whereby measurement of cornea thickness as well as photographing of cornea endothelium can be accomplished.

In the apparatus for obtaining images of a cornea, which is equipped with the means for recording both an eye-front image and an enlarged image of the subject part, it is possible to record an eye-front image by a first focusing detection signal derived from the subject-part focusing detection means and also to record an enlarged image of cornea cells of the subject part by a second focusing detection signal.

In the case of the apparatus for obtaining images of a cornea, which is equipped with the means for recording both an eye-front image and an enlarged image of the subject part, in recording an enlarged photographed image of cornea endothelium cells, it is desirable that reflected light of the position-detection indicator derived from the subject part is brought to a specified position of the eye-front image in the eye-front observation means to accomplish alignment (optical-axis adjustment) and that, thereafter, an eye-front image is recorded by a cornea-epithelium focusing detection signal from the subject-part focusing detection means while an enlarged photographed image of cornea endothelium cells of the subject part is recorded by a cornea-endothelium focusing detection signal.

According to the method for obtaining images of a cornea of the present invention, with the alignment-use indicator light projected toward the subject eye coaxially with the optical axis of the eye-front observation optical system, the eye axis of the subject can be aligned with the optical axis by moving the imaging system so that the light spot on the monitor screen derived from the reflected light from the eyeball surface of the subject eye is brought to a specified position such as the center of the screen. In doing this, even if the position of the light spot varies due to the normally moving eyeball, alignment of the imaging system can be accomplished without fails by eliminating noise light other than the light spot, in a way that while the whole imaging system is automatically moved in a direction perpendicular to the optical axis of the observation optical system, i.e. in the X- and Y-direction, the imaging system is started to move forward so as to track the light spot with the detection range of the light spot narrowed when the light spot comes to a specified area of the screen, i.e. a narrowed area around the specified position (usually, the center of the screen). Then, with the imaging system brought close to the subject eye, the focusing of the enlarged-imaging optical system on the cornea cells is correctly detected by a photo-detector other than that for alignment having its light-receiving surface at such a position on the optical axis of the enlarged-imaging optical system that its optical path is other than that of the TV camera, on which light-receiving surface an enlarged image of the subject part is formed. Thus, an enlarged image of cornea cells of the subject part can be automatically and successfully obtained by the enlarged-imaging optical system.

For photographing, the whole imaging system is brought to a specified position on the screen in a direction perpendicular to the optical axis of the observation optical system, so that the light spot on the monitor screen by the reflected light is brought to a specified position on the screen. When the light spot comes to the specified area of the screen, the whole imaging system is started to move forward so as to track the light spot in the direction for eye examination. The focusing of the enlarged-imaging optical system on the cornea subject part is detected by the photo-detector having its light-receiving surface at such a position on the optical axis of the enlarged-imaging optical system that its optical path is other than that of the TV camera. Thus, an enlarged image of cornea cells of the subject part is obtained. Thereafter, the imaging system is moved in the direction perpendicular to the optical axis of the observation optical system, in such a way that its travel in the Y-direction remains the same and that its travel in the X-direction is canceled. Thus, when one eye of the subject has been completely photographed and then the other eye is to be photographed, the imaging system is only required to move to a less length in the X- and Y-direction, i.e. the frame on which the imaging system is mounted is only required to move to a less length in the Y-direction, due to the fact that the Y and Z values of the right and left eyes are similar to each other. Also, the imaging system is automatically returned to the initial setting side by a specified small distance from the cornea-cells focusing detection position so that the imaging system is put into a standby state. Thus, the travel of the imaging system, i.e. the frame on which the imaging system is mounted, is only required to move to a less length from the standby position to the subject-eye imaging position. As a result, when one eye of the subject has been completely imaged and the other is to be imaged, the operability of the machine can be improved and the imaging is accomplished more quickly.

When an enlarged image of cornea cells of the subject part is obtained by the above-described method, i.e. by bringing the imaging system close to the subject eye and detecting the focusing of the enlarged-imaging optical system on the cornea subject part with a photo-detector other than that for alignment having its light-receiving surface at such a position on the optical axis of the enlarged-imaging optical system that its optical path is other than that of the TV camera, the subject part, whichever cornea endothelium or cornea epithelium, can be photographed as it is enlarged by properly selecting the procedure and conditions for detection of the focusing.

In the apparatus for obtaining images of a cornea according to the present invention, at least an enlarged image of the subject part is formed by the enlarged-imaging optical system based on reflected light derived from the eyeball surface illuminated through the slit by the illuminating system. The imaging system is automatically moved forward by a signal from the focusing-detection use photo-detector having its light-receiving surface at such a position that its optical path is other than that of the imaging surface of the enlarged image of the subject part by the enlarged-imaging optical system. Further, the focusing of the enlarged-imaging optical system on cornea cells such as cornea endothelium cells is correctly detected by the focusing-detection use photo-detector. Then an imaging signal such as a trigger is generated by imaging-signal generating means, whereby an enlarged image of cornea cells of the subject part can be photographed by a strobe light source or the like, successfully.

In the apparatus for obtaining images of a cornea according to the present invention, which is equipped with means for recording an eye-front image and an enlarged image of a subject part, a beam of light of the position-detection indicator used for detecting the position of the photographing site is projected on the subject part toward the subject eye. Reflected light from the subject part is passed through the eye-front observation optical system so that the reflected light is brought to a specified position of an eye-front image in the eye-front observation means. Then the light spot by the reflected light can be recorded together with an eye-front image by the recording means. On the other hand, an enlarged image of the subject part is formed by the enlarged-imaging optical system based on the reflected light derived from the subject part illuminated by the illuminating system. In this image formation, the imaging system is moved forward toward the subject eye manually or automatically so that the focusing of the enlarged-imaging optical system on cornea cells of the subject part is detected by the focusing-detection use photo-detector. Thus, cornea cells of the subject part can be easily photographed by the enlarged-imaging optical system according to a focusing detection signal derived from the subject-part focusing detection means. The enlarged photographed image is recorded along with the eye-front image at which the light spot by the reflected light of the position-detection indicator derived from the subject part is positioned. Thus, a desired enlarged photographed image of cornea cells and an eye-front image showing the photographed site can be simultaneously observed by using proper display means.

If the focusing-detection use photo-detector is so arranged to detect both the cornea epithelium focusing position and the cornea endothelium focusing position of the enlarged-imaging optical system, and if the apparatus for obtaining images of a cornea comprises means for detecting a travel of the imaging system from the cornea epithelium focusing position to the cornea endothelium focusing position both detected by the focusing-detection use photo-detector and further is so arranged as to be capable of measuring cornea thickness as well as photographing cornea endothelium, then the cornea thickness can be measured simultaneously with photographing the cornea endothelium based on the detected travel of the imaging system from the cornea epithelium focusing position to the cornea endothelium focusing position.

Further, in the apparatus for obtaining images of a cornea according to the present invention, which is equipped with means for recording both an eye-front image and an enlarged image of the subject part, an enlarged image of cornea cells of the subject part can be recorded with one TV camera, by programming so that an eye-front image is recorded by a first focusing detection signal from the subject-part focusing detection means and that an enlarged image of cornea cells of the subject part is recorded by a second focusing detection signal. In more detail, in the case of cornea epithelium photographing, alignment is done with a contact lens for use of epithelium photographing loaded on the cornea surface and thereafter, as the optical system moves forward, the focusing-detection use photo-detector first detects reflected light from the surface of the contact lens for use of epithelium photographing and then reflected light of cornea epithelium. Thus, an enlarged image of cornea epithelium cells can be easily photographed along with an eye-front image showing the photographing site of the cornea epithelium.

On the other hand, in the above apparatus, in recording the enlarged photographed image of cornea endothelium cells of the subject part, an eye-front image is recorded by an epithelium focusing detection signal, which is the first focusing detection signal and which can be easily extracted, while an enlarged photographed image of cornea endothelium cells of the subject part is recorded by a cornea endothelium focusing detection signal, which is the second focusing detection signal. With this arrangement, the timing for recording the eye-front image can be set extremely close to the timing for enlarged photographing of the cornea endothelium cells. Thus, positioning accuracy for photographing an enlarged image of the cornea cells of the photographing site shown by the light spot in the eye-front image can be easily improved.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE PREFERRED EMBODIMENTS

Now embodiments of the present invention are described with reference to the accompanying drawings.
[Embodiment 1]

Figure 1:
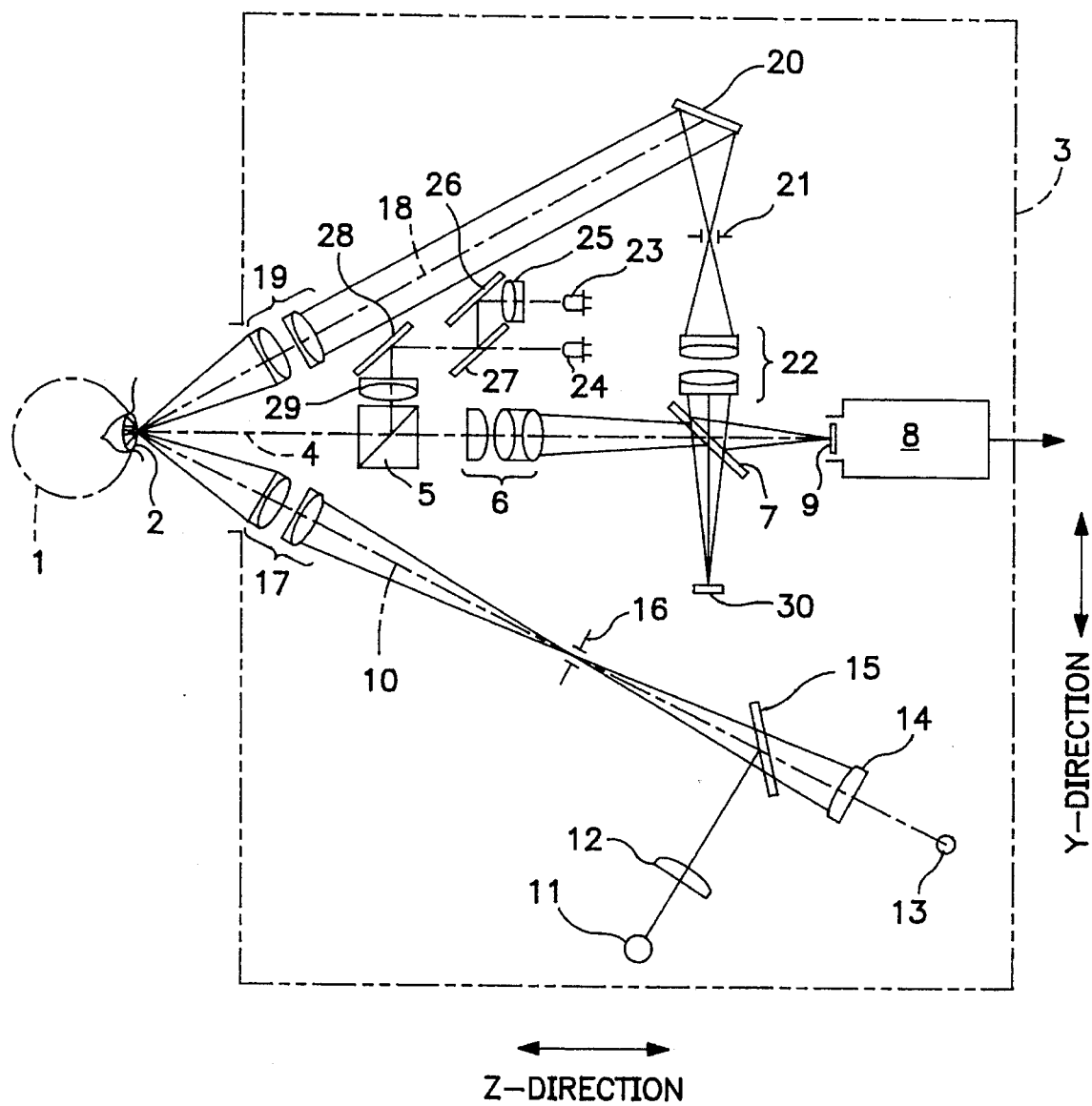
FIG. 1 is an optical path diagram of a first embodiment according to the present invention.
Figure 2:
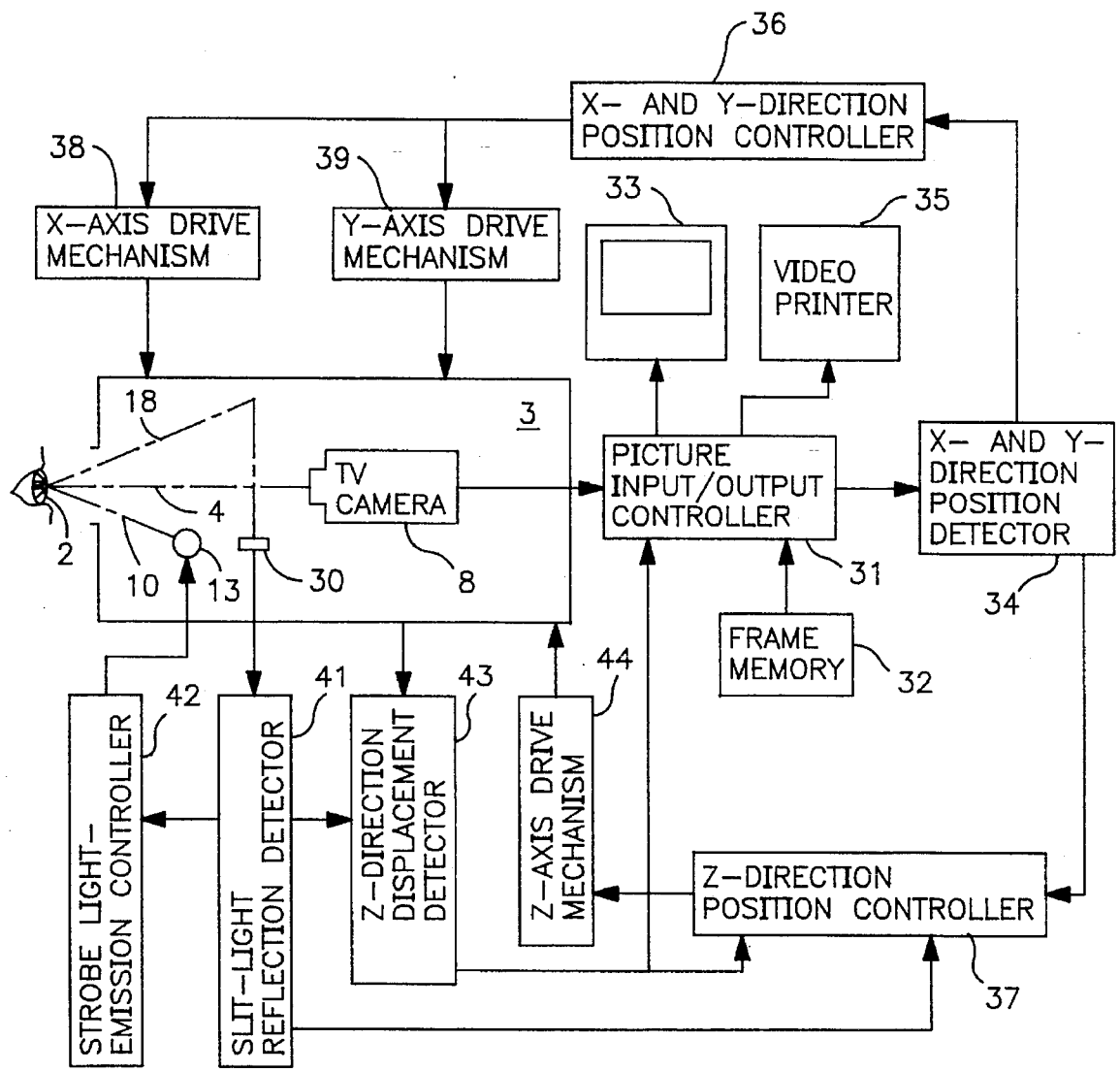
FIG. 2 is a block diagram of the first, second, and third embodiments of the present invention.

FIG. 1 is an optical path diagram of this embodiment, and FIG. 2 is a block diagram of the electrical circuit of the embodiment.

In FIG. 1 there is shown an imaging system 3 which comprises: an illuminating system for illuminating through a slit an eyeball surface 2 of a subject eye 1; an eye-front observation optical system in which alignment-use indicator light for positional adjustment of the imaging optical axis is projected toward the subject eye and the resulting reflected light of cornea is imaged by a TV camera 8; and an enlarged-imaging optical system so arranged as to be capable of enlarged observation or enlarged photographing of the subject part by the TV camera 8 based on the slit illuminating light with which the eyeball surface has been illuminated in opposition to the eyeball surface 2 in a direction different from that in which the observation optical system does. The imaging system 3 is moved in three directions of X-direction that is perpendicular to an optical axis 4 of the eye-front observation optical system and vertical to the sheet surface of the figure, Y-direction that is the longitudinal direction of the sheet surface, and Z-direction that is the direction of the optical axis 4 of the observation optical system, by their corresponding drive mechanisms which will be described later.

As illuminating sources for the subject part of the eyeball surface 2, there are provided an illuminating lamp 11 used to focus the enlarged-imaging optical system and a strobe discharge tube 13 used to photograph an enlarged image of cornea endothelium cells. The illuminating lamp 11 and the strobe discharge tube 13 are arranged in such a way that light from the illuminating lamp 11 has its infrared light reflected by a half mirror (which transmits visible light and reflects infrared light) 15 and that light (visible light) from the strobe discharge tube 13 passes the half mirror 15, each light being focused on the position of a slit 16, whereby the position on which light emitted by the illuminating lamp 11 is focused by a condenser lens 12 and the position on which light emitted by the strobe discharge tube 13 is focused by a condenser lens 14 are coincident with each other. In this case, a visible-light cut filter is inserted into an optical path between the illuminating lamp 11 and the half mirror 15, as required, while an infrared-light cut filter is inserted between the strobe discharge tube 13 and the condenser lens 14. It is also arranged that the light that has passed the slit 16 illuminates obliquely a cornea 2, which is the subject's observation surface, of a subject's eyeball 1 through a projection lens 17 at a specified angle with respect to the eye axis, with illuminating light of the illuminating lamp 11 at the time of focusing and with strobe light at the time of photographing.

The optical system for observing the eye front has, on an eye-front observation optical system optical axis 4 to be positioned on the eye axis, a beam splitter 5, an eye-front picture lens 6, and a half mirror (which transmits infrared light and reflects visible light) 7 crossing the eye-front observation optical system optical axis 4 at 45° at their specified positions in this order from the front. By this arrangement, on a CCD light-receiving surface 9 in front of the TV camera 8 located backward, an eye-front image is formed by the eye-front picture lens 6 while near infrared light for optical axis alignment, which will be described later, is projected and formed into an image.

Also, on the side opposite to an illuminating optical axis 10 of the illuminating system with the eye-front observation optical system optical axis 4 interposed therebetween, there is provided an enlarged-imaging optical system for observing or photographing enlarged images of cornea endothelium cells of the observation part with reflected light of the oblique slitted illuminating rays of light by the illuminating lamp 11 or the strobe discharge tube 13 to the eyeball surface, and moreover for focusing, so that an enlarged photographed image is formed on the CCD light-receiving surface 9 in front of the TV camera 8 and on a focusing-detection use photo-detector 30 which will be described later. In more detail, at specified positions on an optical axis 18 generally symmetrical with the illuminating optical axis 10 of the illuminating system with the eye-front observation optical system optical axis 4 for use of eye front photographing interposed therebetween, an objective lens 19 is disposed on the eyeball surface side and a mirror 20 is disposed at a specified distance from the objective lens 19, so that image rays of light by the reflected light of the above illuminating light from the eyeball surface are bent so as to cross the optical axis 18 at a specified angle and cross the eye-front observation optical system optical axis 4 perpendicularly at a specified position. The image rays of light reflected by the mirror 20 pass a lamp field diaphragm 21 and an image-forming lens 22, where visible light by the strobe light out of the enlarged image rays of light is totally reflected by the half mirror 7 crossing the eye-front observation optical system optical axis 4 at 45°, so that an enlarged photographed image of cornea endothelium cells of the observation surface is formed on the CCD light-receiving surface 9 of the TV camera 8. Further, the infrared light out of the enlarged rays of light passes the half mirror, thus forming an image on the focusing-detection use photo-detector 30.

On the other hand, fixed indicator light for presenting a fixed indicator to the subject and near infrared light, which is alignment light for aligning the eye axis and the optical axis 4 with each other, are applied to the beam splitter 5 on the eye-front observation optical system optical axis 4 from sideway perpendicular to the optical axis 4. Then these rays of light are advanced on the eye-front observation optical system optical axis 4 so as to make incident on the eyeball surface 2. In more detail, at specified positions on the sideway of the eye-front observation optical system, an LED 23 of near infrared light, which is the alignment light, and an LED 24 of blinking visible light, which is the fixed indicator light, are disposed so that optical axes of their respective rays of light are parallel to the optical axis 4 of the observation optical system. The near infrared light from the near-infrared LED 23 passes a condenser lens 25, a mirror 26, a near-infrared-light reflecting and visible-light transmitting mirror 27, a mirror 28, and a condenser lens 29, and is reflected by the reflection surface within the beam splitter 5, thus making incident on the eyeball surface on the eye-front observation optical system optical axis 4. Further, the blinking visible light from the blinking-visible-light LED 24 passes the near-infrared-light reflecting and visible-light transmitting mirror 27, advancing on the eye-front observation optical system optical axis 4 through the mirror 28, the condenser lens 29, and the beam splitter 5 as in the near infrared light, making incident on the eyeball surface 2.

Also, on the optical axis on which the optical axis 18 of the enlarged-imaging optical system is bent by the mirror 20 to cross the eye-front observation optical system optical axis 4 perpendicularly, at a conjugate position with respect to the reflecting surface of the half mirror 7 disposed to cross the eye-front observation optical system optical axis 4 at 45°, there is provided the focusing-detection use photo-detector 30 having a long light-receiving surface in the longitudinal direction of a focusing-detection use image based on the slit illuminating light. By this arrangement, when the imaging system 3, which comprises the eye-front observation optical system, the illuminating system, and the enlarged-imaging optical system, moves toward the subject eye, the focusing-detection use photo-detector 30 will detect both a cornea epithelium focusing position and a cornea endothelium focusing position of the enlarged-imaging optical system.

Then, an image-receiving signal obtained according to an image formed on the CCD light-receiving surface 9, which is the image-forming surface of the TV camera 8, is fed to an image input/output control circuit 31 as shown in FIG. 2. Next, for optical axis positional adjustment, a light spot by the reflected light of the near infrared light for alignment derived from the eyeball surface 2 is displayed on the screen of a monitor display 33 that has received an image signal from the image input/output control circuit 31. This makes it possible to check how the alignment at an early stage of machanical operation has been done.

Figure 3:
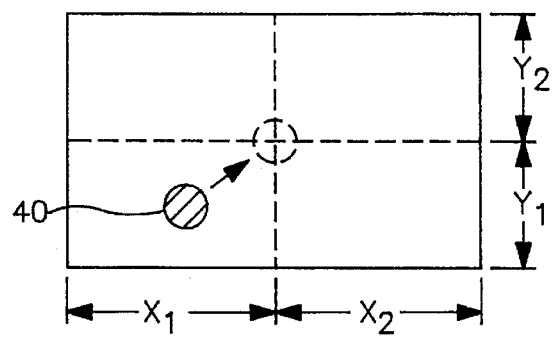
FIG. 3 is an explanatory view showing the positional relation between the monitor screen and a light spot of the alignment-use indicator light by reflected light of cornea.

An X- and Y-direction position detector circuit 34, which has received the electrical signal from the image input/output control circuit 31, detects the position of the light spot of the near infrared light, i.e. the position in the X- and Y-direction of a light spot 40 (see FIG. 3), on the monitor screen, and further feeds this position detection signal to a X- and Y-direction position control circuit 36. Then, an X-axis drive mechanism 38 and a Y-axis drive mechanism 39 are driven so that the light spot 40 on the monitor screen shown in FIG. 3 is positioned at a center of screen that is an intersecting point resulting from equally dividing the screen in the X-direction into two, $X_1$ and $X_2$, and moreover equally dividing the screen in the Y-direction into two, $Y_1$ and $Y_2$, according to a control signal from the position control circuit 36.

When the X- and Y-direction position detector circuit 34 detects that the light spot 40 has entered a specified area surrounding the screen center of the screen, which are is reduced in horizontal and vertical dimensions ($X_1$, $X_2$, $Y_1$, $Y_2$) out of the whole screen, it feeds an electrical signal to a Z-direction position control circuit 37, and a Z-axis drive mechanism 44 is activated by a drive signal from the Z-direction position control circuit 37. Thus, the imaging system 3, or more concretely, the frame on which the imaging system 3 is mounted is started to move forward toward the eyeball surface 2 of the subject eye from its initial standby position. Simultaneously when this forward movement has started, the illuminating lamp 11 is lit so that the eyeball surface 2 is illuminated with infrared slit light, whereby the focusing by the enlarged-imaging optical system is started. During the forward movement of the imaging system 3 toward the subject eye 1, the near-infrared LED 23 for alignment is lit while the visible-light LED 24 is blinked. In this state, the frame on which the imaging system 3 is mounted is driven in the X- and Y-directions so that the light spot 40 for alignment on the monitor screen by the reflected light from the eyeball surface 2 of the subject eye that is normally moving comes to the center of the screen, while the imaging system 3 tracks the intersecting point on the screen.

As the imaging system 3 moves forward toward the subject eye 1, enlarged image rays of light (infrared rays) by the reflected light from the eyeball surface 2 of the subject eye enter the focusing-detection use photo-detector 30 from the enlarged-imaging optical system, while a light-receiving signal from the photo-detector 30 enters a slit-light reflection detector circuit 41, whereby cornea epithelium focusing detection and cornea endothelium focusing detection are successively carried out. When this cornea endothelium focusing has been detected, the signal from the slit-light reflection detector circuit 41 enters the Z-direction position control circuit 37, so that the Z-axis drive mechanism 44 stops the movement of the imaging system 3 according to a signal from the control circuit 37. At the same time, a strobe-light-emission control circuit 42 is activated by a signal from the slit-light reflection detector circuit 41, so that the strobe discharge tube 13 emits light (where the near-infrared LED 23 is off over alignment), and the reflected light from the eyeball surface 2 passes the optical path of the enlarged-imaging optical system so that an enlarged image of the subject part is formed on the light-receiving surface 9 of the TV camera 8. The image signal of the enlarged image of the cornea endothelium cells of the subject part derived from the TV camera 8 is written from the image input/output control circuit 31 into a frame memory 32, while the enlarged image 47 is displayed on the monitor display 33. Also, this enlarged image of cornea endothelium cells can be read from the frame memory 32 by the image input/output control circuit 31 as required, and printed out by a video printer 35, allowing a video print of the subject eye to be attached to the medical sheet.

On the other hand, as the imaging system 3 moves forward, its forward travel is sequentially detected by a Z-direction travel detector 43 including a rotation-amount detector, such as a rotary encoder, connected to the Z-axis. Also, from the cornea epithelium focusing detection signal and the cornea endothelium focusing detection signal that have successively fed to the Z-direction travel detector 43 from the slit-light reflection detector circuit 41, the travel of the imaging system 3 from the cornea epithelium focusing position to the cornea endothelium focusing position is calculated within the detector 43. A signal of the calculated travel, i.e. of cornea thickness, is displayed on the monitor display 33 via the image input/output control circuit 31 as a cornea thickness along with the enlarged image of the cornea endothelium cells.

When the above photographing has been completed, the imaging system 3 is automatically returned to its standby position. More specifically, when the photographing is completed, the X-axis drive mechanism 38 and the Z-axis drive mechanism 44 are activated while the Y-axis drive mechanism 39 is not activated, according to control signals transferred from the X- and Y-direction position control circuit 36 and the Z-direction position control circuit 37 from the image input/output control circuit 31 via the X- and Y-direction position detector circuit 34. As a result, the imaging system 3 is driven to its initial neutral position in the X-direction, and inversely driven along the Z-axis in the Z-direction so that a specified small distance from the cornea endothelium focusing detection position, i.e. a distance more than the average cornea thickness of 0.5 mm is detected by a travel detection signal involved in the return of the illuminating system from the Z-direction travel detector 43, and the drive is controlled via the Z-direction position control circuit 37 is returned toward the initial setting side, thus putting the-imaging system 3 into its standby state. By this arrangement, when one eye of the subject is finished being examined and the other eye is to be examined, the imaging system 3 is required to move only a short distance in both the Y- and Z-direction since the Y-value and Z-value of right and left eyes are similar to each other. As a result, operational load of the apparatus can be reduced and the examination time can be reduced.

Figure 4:
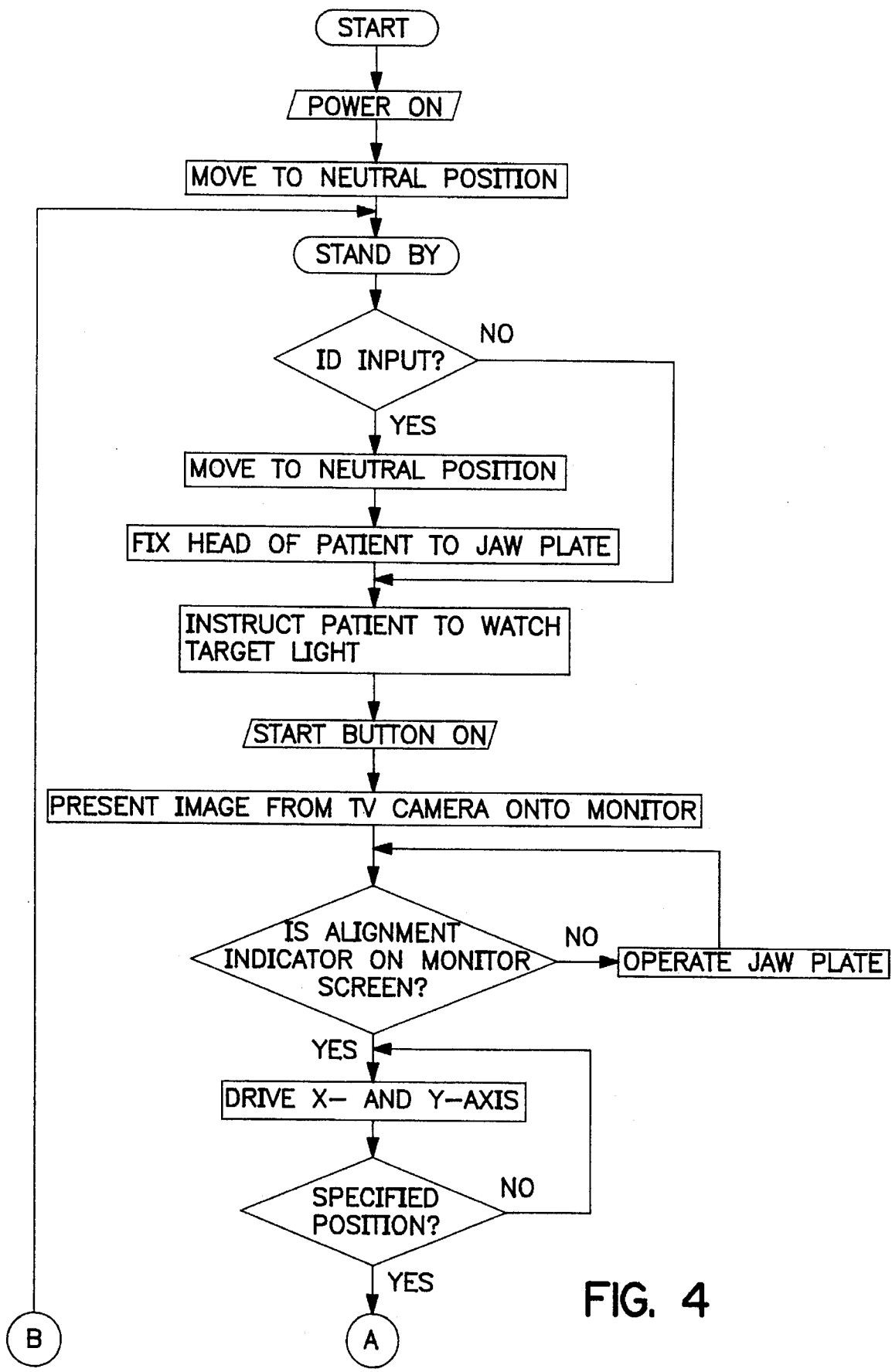
FIG. 4 is a flow chart showing the early-stage procedure for cornea cell photographing in each embodiment of the present invention.
Figure 5:
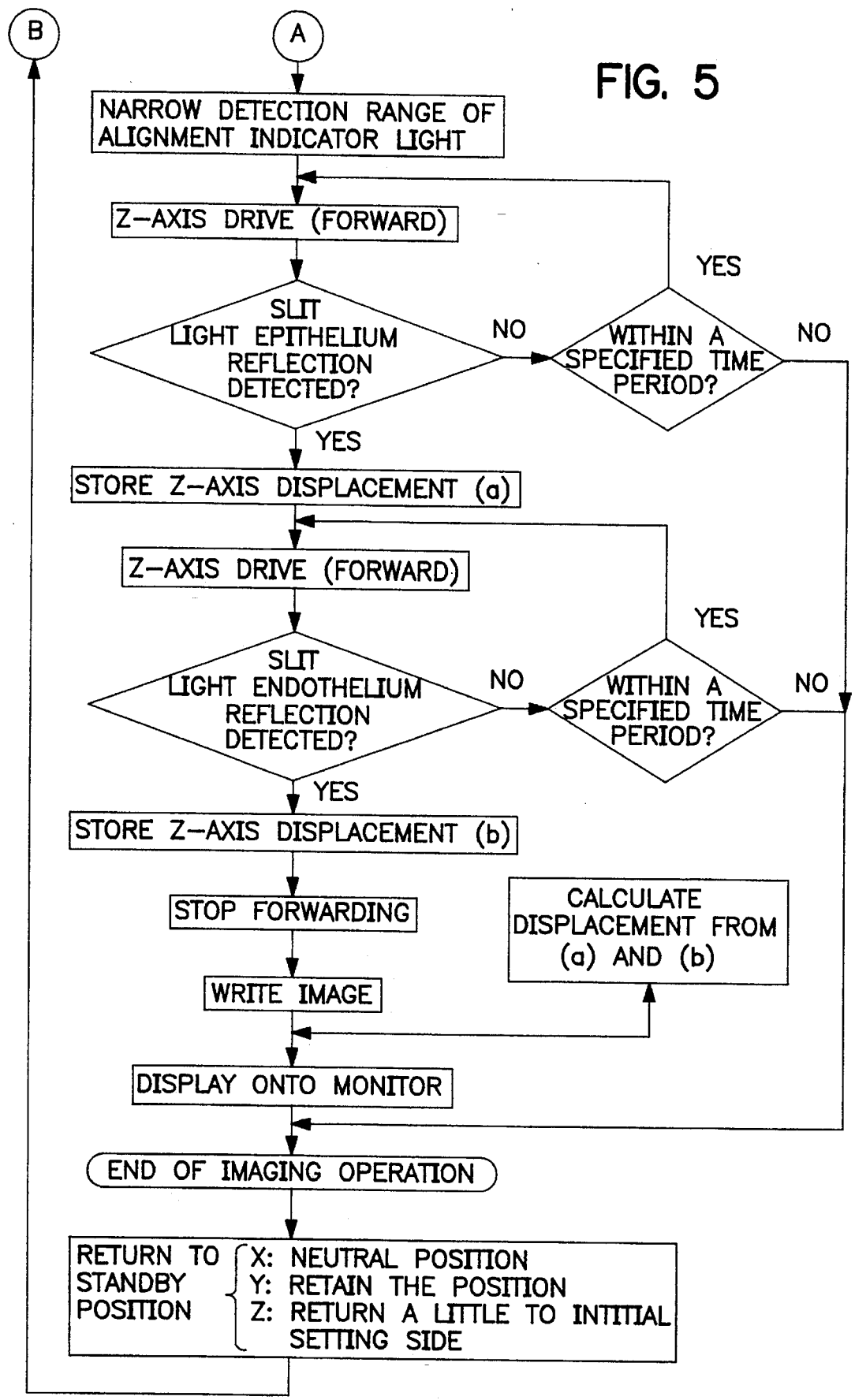
FIG. 5 is a flow chart showing the procedure that is subsequent to FIG. 4 in the case of cornea cell photographing in the first embodiment of the present invention.

Next, the operating procedure of the apparatus for obtaining images of a cornea according to the present invention is described based on the flow charts as shown in FIG. 4 and FIG. 5.

First, the apparatus for obtaining images of a cornea is powered on, so that the illuminating system, which is the imaging system 3, is moved from an abnormal position due to power failure or the like to its normal position, which is a neutral position, thus being brought into a standby state. When the subject changes and is replaced by another person, his or her ID card number is entered into the apparatus. Then, with confirmation of the movement of the optical system, i.e. the imaging system 3, to its neutral position, the head of the subject is fixed on the jaw plate, which is not shown. Alternatively, with the subject unchanged, when one eye of the subject is finished being photographed and the other eye is to be photographed, it is unnecessary to enter the ID card into the apparatus, in which case the head of the subject is already fixed on the jaw plate.

Next, for alignment, the near-infrared LED 23 and the visible-light LED 24 are lit, and the subject is instructed to fixedly view the blinking visible light from the visible-light LED 24, which is a fixed indicator, where the start button is pressed (in this case, the subject cannot see the alignment-use indicator light from the near-infrared LED 23). Then, the monitor display 33 (hereinafter referred to as monitor 33) is made to present an eye-front image from the TV camera 8. Whereas the monitor 33 is displaying a light spot, which is a cornea reflection image of the alignment-use indicator light, in the normal state, if no light spot is presented on the monitor 33, the light spot is made to come onto the monitor 33 by operating the jaw plate to adjust its height or by other operation. Automatically, or by pressing the start button when the light spot of alignment-use indicator light is presented on the monitor 33, the X- and Y-axes are driven to move the imaging system 3 with respect to the subject eye, depending on the position of the light spot the position of which has been detected by the X- and Y-direction position detector circuit 34, whereby the light spot is moved to the specified position (center) on the screen.

When the light spot has come to around the specified center in this way, the detection range of the alignment indicator reflected light on the monitor screen is narrowed so that noise light is prevented from mixing in the subsequent alignment. Then with alignment effected within the narrowed range, the Z-axis is driven to make the imaging system 3 move forward. During this forward movement of the imaging system 3, reflection of the slit light from the cornea epithelium is detected by the slit-light reflection detector circuit 41. When epithelium reflection is detected, a travel in the Z-axis direction (a) is stored in the Z-direction travel detector 43. In this case, with no epithelium reflection detected, detection of the epithelium reflection is continued if the reflection detection is within a specified time period since the light spot has entered the specified position on the monitor screen. However, if no signal enters the specified position when the specified time has elapsed, there would be malfunction so that the imaging system 3 should be returned to a standby position, which will be described later, without photographing, and the procedure should be redone. In such a case, the imaging system 3 is to be returned to the initial neutral position by a signal from an unshown limit switch provided for the Z-axis motion amount.

Then, the imaging system 3 continues moving forward by Z-axis drive. Also, the slit light reflection from the cornea endothelium is detected by the slit-light reflection detector circuit 41. When the endothelium reflection has been detected, the then resulting Z-axis travel (b) is stored in the Z-direction travel detector 43, where the Z-axis drive is stopped so that the imaging system 3 is stopped from moving forward, by a signal of the endothelium reflection detection. At the same time, with strobe light emitted, photographing is done with the TV camera 8, and an image is written into the frame memory 32. Then from the Z-axis travel (a) for epithelium detection and the X-axis travel (b) for endothelium detection, the cornea thickness is calculated by the Z-direction travel detector 43, where the then resulting Y value (height) is stored in the X- and Y-direction position detector circuit 34, and the photographed enlarged image of cornea endothelium cells and the cornea thickness are displayed on the monitor 83. Thus, the photographing is completed. On the other hand, when endothelium reflection by the slit light has not been detected, the endothelium reflection detection can be continued if the reflection detection is within a specified time period since the light spot has entered the specified position on the monitor screen. However, if a specified time has elapsed since then, there would be malfunction, so that the imaging system 3 should be returned to a standby state, which will be described later, and the procedure should be redone. This is also the case with the foregoing epithelium reflection.

After photographing, the imaging system 3 is automatically returned to the standby position in the X-, Y-, and Z-directions, thus put into standby state. In this process, the movement in the X-direction of the imaging system 3, i.e. rightward and leftward with respect to the optical axis 4, is such that the imaging system 3 is returned to the neutral position, which is the operation center. The movement in the Y-direction of the imaging system 3, i.e. upward and leftward with respect to the optical axis 4, is such that the height represented by the Y value at the time when reflection of slit light from the endothelium is detected is used as it is. The movement in the Z-direction, i.e. forward and backward, is such that the imaging system 3 is moved back a little toward the initial setting position from the (a) position where the reflection of slit light from the epithelium has been detected. Thus, with the subject unchanged, since his or her Y value and Z value are similar to each other, the imaging system is required to move to a less extent when the photographing is done with the eye changed, allowing the photographing to be carried out more quickly. It is to be noted that when the subject has changed, his or her ID card number is entered into the apparatus and the imaging system 3 is moved to the neutral position in the Y- and Z-direction.

[Embodiment 2]

A second embodiment of the present invention is described below, taking a case where cornea endothelium is photographed and at the same time its photographed site is displayed.

Figure 6:
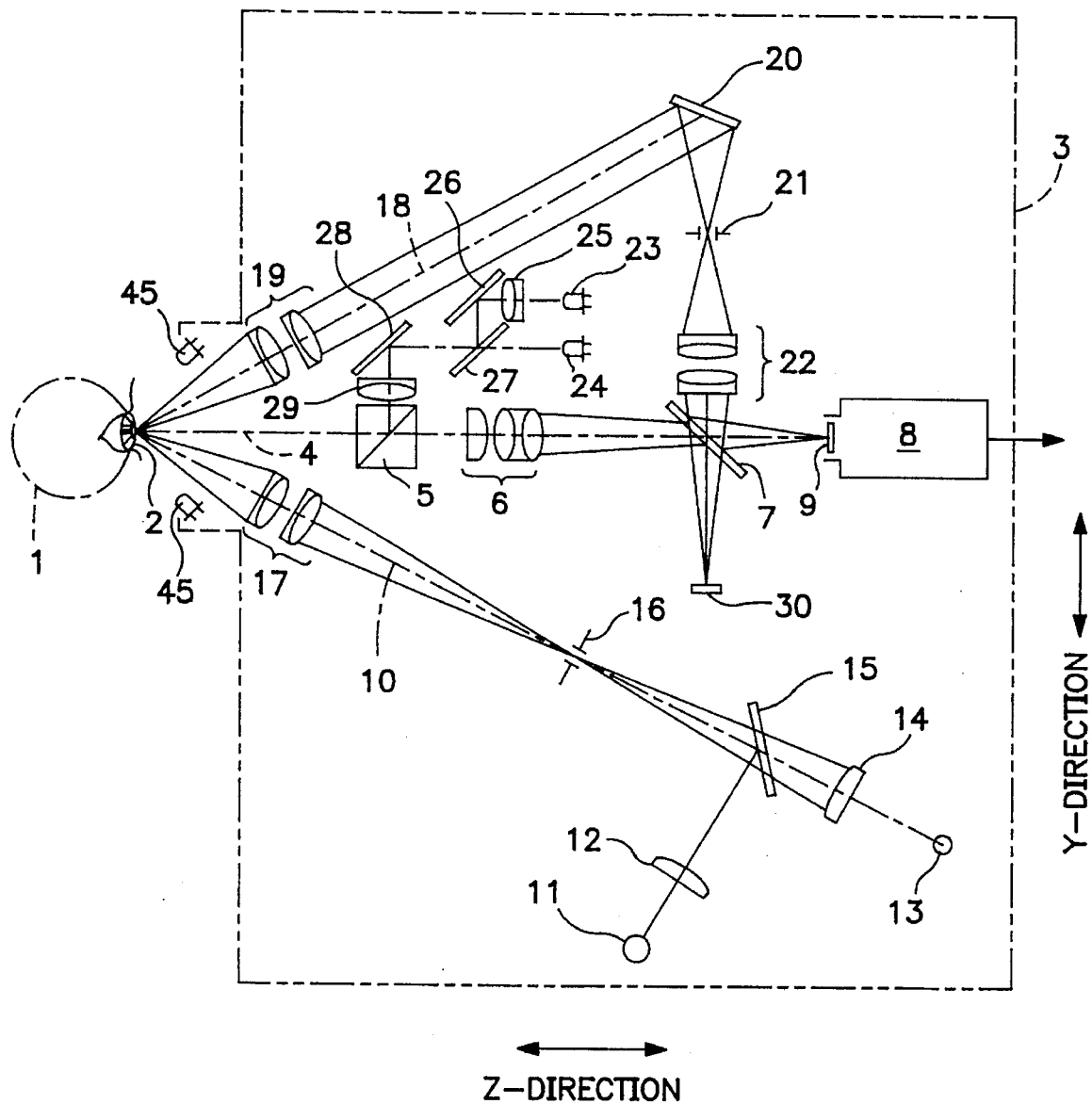
FIG. 6 is an optical path diagram of the second and third embodiments of the present invention.

FIG. 6 is an optical path diagram of the second embodiment, wherein an eye-front illuminating light source is added to the optical path diagram of the embodiment of FIG. 1. The block diagram of electrical circuit of the second embodiment is the same as that of the first embodiment (FIG. 2), and this diagram is used here also.

In FIG. 6 there is shown an imaging system 3 which comprises: an illuminating system for illuminating through a slit an eyeball surface 2 of a subject eye 1; an eye-front observation optical system in which alignment-use indicator light both for positional adjustment of the imaging optical axis and for display of imaging position at the time of photographing is projected toward the subject eye and the resulting reflected light from the subject part is imaged by a TV camera 8, and in which an eye-front illuminating light source is added for use of displaying the eye front to show the site of photographing; and an enlarged-imaging optical system so arranged as to be capable of enlarged observation or enlarged photographing of the subject part by the TV camera 8 based on the slit illuminating light with which the eyeball surface has been illuminated in opposition to the eyeball surface 2 in a direction different from that in which the observation optical system does. The imaging system 3 is moved in three directions of X-direction that is perpendicular to an optical axis 4 of the eye-front observation optical system and vertical to the sheet surface of the figure, Y-direction that is the longitudinal direction of the sheet surface, and Z-direction that is the direction of the optical axis 4 of the observation optical system, by their corresponding drive mechanisms, as has been the case also with the first embodiment.

The arrangement of an illuminating lamp 11 and a strobe discharge tube 13, which are illuminating sources for the subject part of the eyeball surface 2, as well as the arrangement of condenser lenses 12, 14, a half mirror (which transmits visible light and reflects infrared light) 15, a slit 16, a projection lens 17, and the like are the same as in the first embodiment. Light that has passed the slit 16 illuminates obliquely a cornea 2, which is the subject's observation surface, of a subject's eyeball 1 through a projection lens 17 at a specified angle with respect to the eye axis, with illuminating light of the illuminating lamp 11 at the time of focusing by the enlarged-imaging optical system and with strobe light by the strobe discharge tube 13 at the time of enlarged photographing of cornea cells.

The optical system for observing the eye front has, at specified positions on an eye-front observation optical system optical axis 4 to be positioned on the eye axis, a beam splitter 5, an eye-front picture lens 6, and a half mirror (which transmits infrared light and reflects visible light) 7 disposed in this order. By this arrangement, on a CCD light-receiving surface 9 in front of the TV camera 8 located backward, an eye-front image is formed by the eye-front picture lens 6 while near infrared light for display of the position of the subject part as well as for optical axis alignment of the apparatus, which will be described later, is projected and formed into an image. Further in this embodiment, there are also arranged infrared LEDs 45, 45 so as to illuminate the eye front from sideway in front of the optical axis 4 of the eye-front observation optical system, thus making it possible to photograph an eye-front image where the light spot for alignment, which will be described later, is positioned.

Also, at specified positions on an optical axis 18 generally symmetrical with the illuminating optical axis 10 of the illuminating system with the eye-front observation optical system optical axis 4 for use of eye front photographing interposed therebetween, an objective lens 19 and a mirror 20 are disposed so that image rays of light by the reflected light of the above illuminating light from the eyeball surface are bent so as to cross the optical axis 18 at a specified angle and cross the eye-front observation optical system optical axis 4 perpendicularly at a specified position. The image rays of light reflected by the mirror 20 pass a lamp field diaphragm 21 and an image-forming lens 22, where visible light by the strobe light out of the enlarged image rays of light is totally reflected by the half mirror 7 crossing the eye-front observation optical system optical axis 4 at 45°, so that an enlarged photographed image of cornea cells of the observation surface is formed on the CCD light-receiving surface 9 of the TV camera 8. Further, the infrared light out of the enlarged rays of light passes the half mirror, thus forming an image on a focusing-detection use photo-detector 30.

On the other hand, at specified positions on the sideway of the eye-front observation optical system, an LED 23 of near infrared light, which serves as position display light as well as alignment light, and an LED 24 of blinking visible light, which is the fixed indicator light, are disposed for use of alignment and fixed indicator instruction. The near infrared light from the near-infrared LED 23 passes a condenser lens 25, a mirror 26, a near-infrared-light reflecting and visible-light transmitting mirror 27, a mirror 28, and a condenser lens 29, and is reflected by the reflection surface within the beam splitter 5, thus making incident on the eyeball surface on the eye-front observation optical system optical axis 4. Further, the blinking visible light from the blinking-visible-light LED 24 passes the near-infrared-light reflecting and visible-light transmitting mirror 27, advancing on the eye-front observation optical system optical axis 4 through the mirror 28, the condenser lens 29, and the beam splitter 5 as in the near infrared light, making incident on the eyeball surface 2.

Also, on the optical axis on which the optical axis 18 of the enlarged-imaging optical system is bent by the mirror 20 to cross the eye-front observation optical system optical axis 4 perpendicularly, at a conjugate position with respect to the reflecting surface of the half mirror 7 disposed to cross the eye-front observation optical system optical axis 4 at 45°, there is provided the focusing-detection use photo-detector 30 for detecting the focusing on the subject part based on the slit illuminating light. When the imaging system 3, which comprises means for projecting the near infrared light serving as both position display light and alignment-use indicator light, and visible light of the fixed indicator onto the subject eye, the eye-front observation optical system, the illuminating system, and the enlarged-imaging optical system, moves toward the subject eye, the focusing-detection use photo-detector 30 will detect a cornea cell focusing position of the enlarged-imaging optical system.

Then, an image-receiving signal obtained according to an image formed on the CCD light-receiving surface 9, which is the image-forming surface of the TV camera 8, is fed to an image input/output control circuit 31 as shown in FIG. 2, in the same way as in the first embodiment. Next, for optical axis positional adjustment, a light spot by the near infrared light for alignment derived from the eyeball surface 2 is displayed on the screen of a monitor display 33 that has received an image signal from the image input/output control circuit 31. This makes it possible to check how the alignment at an early stage of mechanical operation has been done.

The imaging system 3 is controlled and driven by an electrical circuit as shown in FIG. 2 in the same way in the first embodiment, all except the lighting of the infrared LEDs 45, 45 for use of illuminating the eye front for display of a photographed site. In more detail, the position of a light spot 40 (see FIG. 3) in the X- and Y-direction by the near infrared light on the monitor screen is detected by the X- and Y-direction position detector circuit 34. Then, according to a control signal from the X- and Y-direction position control circuit 36 that has received a position detection signal resulting from the above position detection, an X-axis drive mechanism 38 and a Y-axis drive mechanism 39 are driven so that the light spot 40 on the monitor screen shown in FIG. 3 is positioned at a center of screen. When the light spot 40 has come to around the specified center, the detection range of the light spot is reduced at the X- and Y-direction position detector circuit 34 to prevent noise light from mixing, an electrical signal is entered into the Z-direction position control circuit 37 to activate the Z-axis drive mechanism 44 with a drive signal from the circuit 37, and the imaging system 3, more concretely the frame on which the imaging system 3 is mounted, is started to move forward toward the eyeball surface 2 of the subject eye from its initial standby position. During this forward movement, the near-infrared LED 23 for alignment is lit while the visible-light LED 24 is blinked. In this state, the frame on which the imaging system 3 is mounted is driven in the X- and Y-directions so that the light spot 40 for alignment on the monitor screen by the reflected light from the subject part of the eyeball that is normally moving comes to the center of the screen, while the imaging system 3 tracks the light spot 40 on the screen.

Meanwhile, after the light spot 40 has come to around the center of the monitor screen, the infrared LEDs 45, 45 that are arranged so as to illuminate the eye front from outward of the optical paths of the illuminating system and the enlarged-imaging optical system with the optical axis 4 of the eye-front observation optical system interposed therebetween in front of the imaging system 3 instantaneously light, recording an eye-front image as well as the light spot on the monitor screen into a frame memory 32 via the image input/output control circuit 31.

Figure 7:
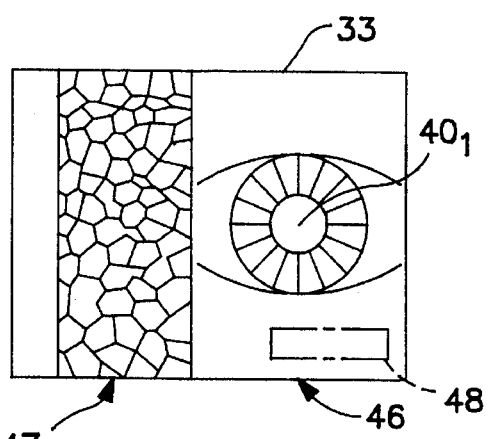
FIG. 7 is a view of the monitor screen on which both an detection image of cornea cells and an eye-front image showing the photographing site by the light spot are displayed.

As the imaging system 3 moves forward toward the subject eye 1, enlarged image rays of light (infrared rays) by the reflected light from the eyeball surface 2 of the subject eye enter the focusing-detection use photo-detector 30 from the enlarged-imaging optical system, while a light-receiving signal from the photo-detector 30 enters a slit-light reflection detector circuit 41, whereby a first focusing detection of cornea epithelium or the like and a second focusing detection of cornea endothelium or the like are successively carried out. When the second focusing on cornea cells or the like has been detected, the signal from the slit-light reflection detector circuit 41 enters the Z-direction position control circuit 37, so that the Z-axis drive mechanism 44 stops the movement of the imaging system 3 according to a signal from the control circuit 37. At the same time, a strobe-light-emission control circuit 42 is activated by a signal from the slit-light reflection detector circuit 41, so that the strobe discharge tube 13 emits light, and the reflected light from the subject part passes the optical path of the enlarged-imaging optical system so that an enlarged image of the subject part is formed on the light-receiving surface 9 of the TV camera 8. The image signal of the enlarged image of the cornea cells of the subject part derived from the TV camera 8 is written from the image input/output control circuit 31 into a frame memory 32, while the eye-front image where the light spot 40 showing the photographing site previously written into the frame memory 32 is positioned as well as the enlarged image are displayed on the monitor 33 (see FIG. 7). Also, this enlarged image of cornea cells and the eye-front image in which the light spot is positioned at the subject site can be read from the frame memory 32 by the image input/output control circuit 31 as required, and printed out by a video printer 35, allowing a video print of the cornea cells of the subject eye showing the photographing site to be attached to the medical sheet. When the eye-front image in which the light spot is positioned at the subject site is displayed onto the monitor 33 in the above-described process, a subject-site marker such as a cross generated by the image input/output control circuit 31 in correspondence to the position of the light spot may be displayed so as to superimpose on the screen, so that the light spot can be discriminated from any other confusing reflected light and the subject site can be emphasized for an easier understanding.

It is to be noted that the alignment light, i.e. position display light may be put out at the time of recording the eye-front image, as required.

On the other hand, as the imaging system 3 moves forward, its forward travel is continuously detected by a Z-direction travel detector 43 including a rotation-amount detector, such as a rotary encoder, connected to the Z-axis. Also, when the cornea endothelium focusing is detected by the focusing-detection use photo-detector 30, from the cornea epithelium focusing detection signal and the cornea endothelium focusing detection signal that have successively fed to the Z-direction travel detector 43 from the slit-light reflection detector circuit 41, the travel of the imaging system 3 from the cornea epithelium focusing position to the cornea endothelium focusing position is calculated within the detector 43. A signal of the calculated travel, i.e. of cornea thickness, is displayed on the monitor display 33 via the image input/output control circuit 31 as a cornea thickness along with the enlarged image of the cornea endothelium cells.

When the above photographing has been completed, the imaging system 3 is automatically returned to its standby position. More specifically, when the photographing is completed, the X-axis drive mechanism 38 and the Z-axis drive mechanism 44 are activated while the Y-axis drive mechanism 39 is not activated, according to control signals transferred from the X- and Y-direction position control circuit 36 and the Z-direction position control circuit 37 from the image input/output control circuit 31 via the X- and Y-direction position detector circuit 34. As a result, the imaging system 3 is driven to its initial neutral position in the X-direction, and inversely driven along the Z-axis in the Z-direction so that a specified small distance from the cornea endothelium focusing detection position, i.e. a distance more than the average cornea thickness of 0.5 mm, in the case of detection of cornea endothelium focusing, or a specified small distance (i.e. a small distance more than the thickness of the contact lens loaded on the cornea epithelium for detection of epithelium focusing) in the case of detection of cornea epithelium focusing is detected by a travel detection signal involved in the return of the illuminating system from the Z-direction travel detector 43, and the drive is controlled via the Z-direction position control circuit 37 is returned toward the initial setting side, thus putting the imaging system 3 into its standby state. By this arrangement, when one eye of the subject is finished being examined and the other eye is to be examined, the imaging system 3 is required to move only a short distance in both the Y- and Z-direction since the Y-value and Z-value of right and left eyes are similar to each other. As a result, operational load of the apparatus can be reduced and the examination time can be reduced, as has been the case also with the first embodiment.

Figure 8:
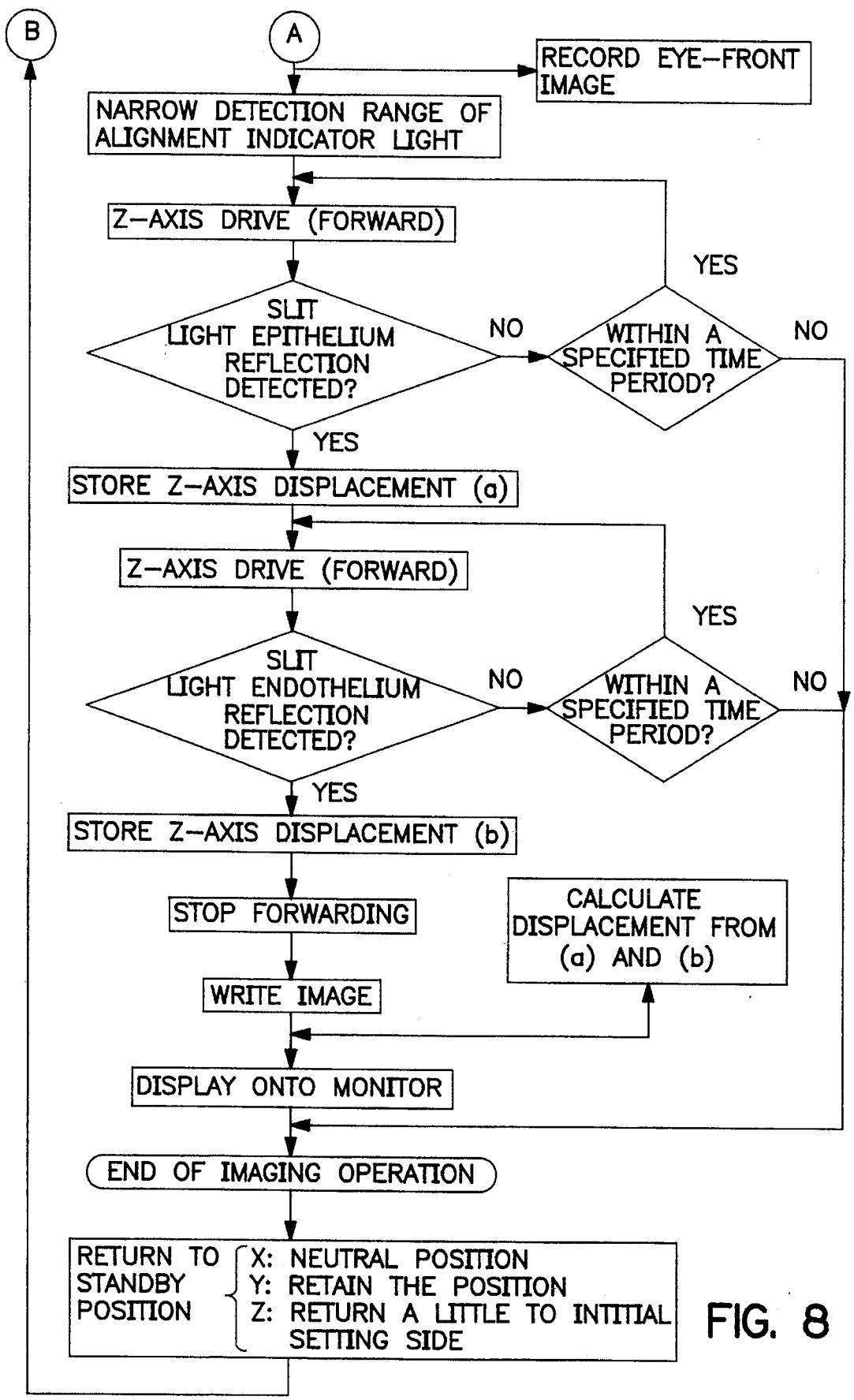
FIG. 8 is a flow chart showing the procedure subsequent to FIG. 4 in the case of cornea endothelium photographing in the second embodiment of the present invention.

Next, the operating procedure for photographing enlarged images of the cornea endothelium cells of the subject part by using this apparatus for obtaining images of a cornea is described based on the flow charts as shown in FIG. 4 and FIG. 8.

First, the apparatus for obtaining images of a cornea is powered on, so that the illuminating system, which is the imaging system 3, is moved from an abnormal position due to power failure or the like to its normal position, which is a neutral position, thus being brought into a standby state. When the subject changes and is replaced by another person, his or her ID card number is entered into the apparatus. Then, with confirmation of the movement of the optical system, i.e. the imaging system 3, to its neutral position, the head of the subject is fixed on the jaw plate, which is not shown. Alternatively, with the subject unchanged, when one eye of the subject is finished being photographed and the other eye is to be photographed, it is unnecessary to enter the ID card into the apparatus, in which case the head of the subject is already fixed on the jaw plate.

Next, for alignment, the near-infrared LED 23 and the visible-light LED 24 are lit, and the subject is instructed to fixedly view the blinking visible light from the visible-light LED 24, which is a fixed indicator, where the start button is pressed (in this case, the subject cannot see the alignment-use indicator light, which also serves for display of the subject site, from the near-infrared LED 23). Then, the monitor 33 is made to present an eye-front image from the TV camera 8. Whereas the monitor 33 is displaying a light spot, which is a cornea reflection image of the alignment-use indicator light that also serves for the position display, in the normal state, if no light spot is presented on the monitor 33, the light spot is made to come onto the monitor 33 by operating the jaw plate to adjust its height or by other operation. Automatically, or by pressing the start button when the light spot is presented on the monitor 33, the X- and Y-axes are driven to move the imaging system 3 with respect to the subject eye, depending on the position of the light spot the position of which has been detected by the X- and Y-direction position detector circuit 34, whereby the light spot is moved to the specified position (center) on the screen.

When the light spot has come to around the specified center in this way, the infrared LEDs 45, 45 arranged so as to illuminate the eye front from sideway in front of the optical axis 4 of the eye-front observation optical system of the imaging system 3 are instantaneously lit, where the eye-front image in which the alignment-use light spot that serves also for the display of position on the monitor screen is positioned is written into the frame memory 32. At the same time, the detection range of the indicator reflected light on the monitor screen is narrowed, so that noise light is prevented from mixing in the subsequent alignment. Then with alignment effected within the narrowed range, the Z-axis is driven to make the imaging system 3 move forward. During this forward movement of the imaging system 3, reflection of the slit light from the cornea epithelium is detected by the slit-light reflection detector circuit 41. When epithelium reflection is detected, a travel in the Z-axis direction (a) is stored in the Z-direction travel detector 43. In this case, with no epithelium reflection detected, detection of the epithelium reflection is continued if the reflection detection is within a specified time period since the light spot has entered the specified position on the monitor screen. However, if no signal enters the specified position when the specified time has elapsed, there would be malfunction so that the imaging system 3 should be returned to a standby position, which will be described later, without photographing, and the procedure should be redone. In such a case, the imaging system 3 is to be returned to the initial neutral position by a signal from an unshown limit switch provided for the Z-axis motion amount. Furthermore, if the fixed indicator is so arranged as to be kept continuously lit during alignment and switched from continuously lighting to blinking when the light spot has come to around the specified position, where the imaging system 3 starts to move forward, then the subject can be informed of the fact that the apparatus has entered a preparation for photographing, so as to be prompted for fixed viewing with his or her subject eye stabilized.

Then, the imaging system 3 continues moving forward by Z-axis drive. Also, the slit light reflection from the cornea endothelium is detected by the slit-light reflection detector circuit 41. When the endothelium reflection has been detected, the then resulting Z-axis travel (b) is stored in the Z-direction travel detector 43, where the Z-axis drive is stopped so that the imaging system 3 is stopped from moving forward, by a signal of the endothelium reflection detection. At the same time, with strobe light emitted, photographing is done with the TV camera 8, and an image of the enlarged cornea endothelium cell image is written into the frame memory 32. Then from the Z-axis travel (a) for epithelium detection and the X-axis travel (b) for endothelium detection, the cornea thickness is calculated by the Z-direction travel detector 43, where the then resulting Y value (height) is stored in the X- and Y-direction position detector circuit 34, and the photographed enlarged image of cornea endothelium cells and the eye-front image which has previously photographed and written into the memory 32 and in which the light spot $40_1$ by the cornea reflected light of the position detection indicator is positioned are displayed on the monitor At the same time, further, the cornea thickness is displayed in a numerical data display section 48, which is part of the monitor screen by an unshown means. Thus, the photographing is completed (see FIG. 7). On the other hand, when endothelium reflection by the slit light has not been detected, the endothelium reflection detection can be continued if the reflection detection is within a specified time period since the light spot has entered the specified position on the monitor screen. However, if a specified time has elapsed since then, there would be malfunction, so that the imaging system 3 should be returned to a standby state, which will be described later, and the procedure should be redone. This is also the case with the foregoing epithelium reflection.

It is to be noted that although the timing at which the infrared LEDs 45, 45 instantaneously light for photographing and recording an eye-front image has been the time of completion of the alignment when the light spot 40 on the monitor screen by the cornea reflected light of the alignment-use indicator light has come to around the specified center in the above-described case, yet of course the timing may be within the time duration after the completion of alignment until the detection of cornea endothelium focusing. The timing of recording the eye-front image is desirably close to the time of photographing the enlarged image. Since the thickness is as small as approximately 0.5 mm, it is advantageous to effect the photographing and recording with a epithelium detection signal by the focusing-detection use photo-detector.

After photographing, the imaging system 3 is automatically returned to the standby position in the X-, Y-, and Z-directions, thus put into standby state. In this process, the movement in the X-direction of the imaging system 3, i.e. rightward and leftward with respect to the optical axis 4, is such that the imaging system 3 is returned to the neutral position, which is the operation center. The movement in the Y-direction of the imaging system 3, i.e. upward and leftward with respect to the optical axis 4, is such that the height represented by the Y value at the time when reflection of slit light from the endothelium is detected is used as it is. The movement in the Z-direction, i.e. forward and backward, is such that the imaging system 3 is moved back a little toward the initial setting position from the (a) position where the reflection of slit light from the epithelium has been detected. This operation is the same as in the first embodiment.

[Embodiment 3]

Figure 10:
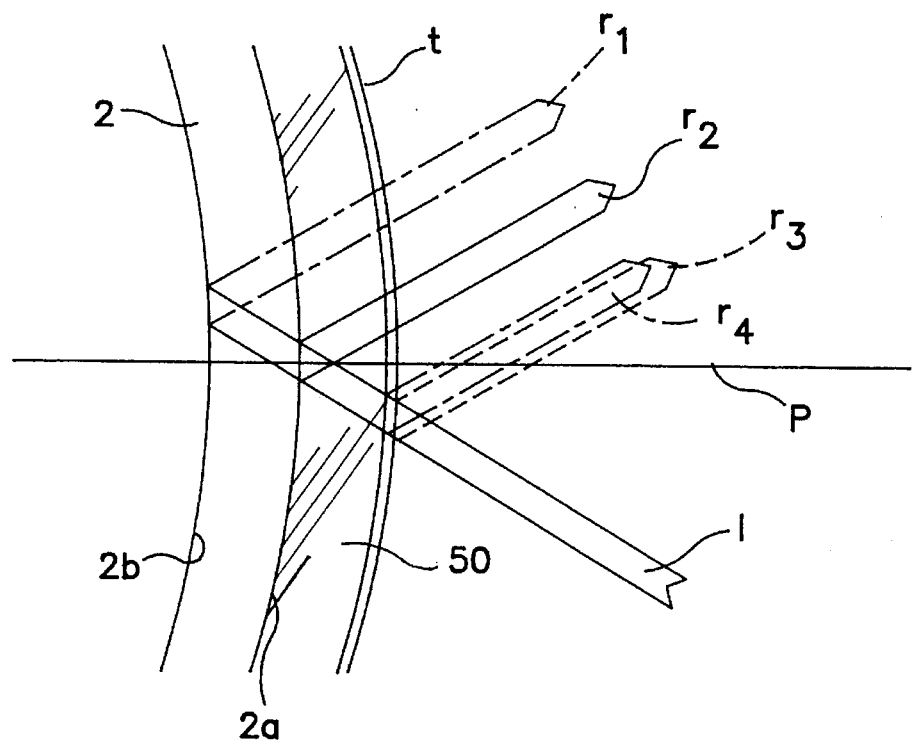
FIG. 10 is an optical path diagram of reflected light of cornea with a contact lens for use of epithelium photographing loaded, by the slit illuminating light.
Figure 11:
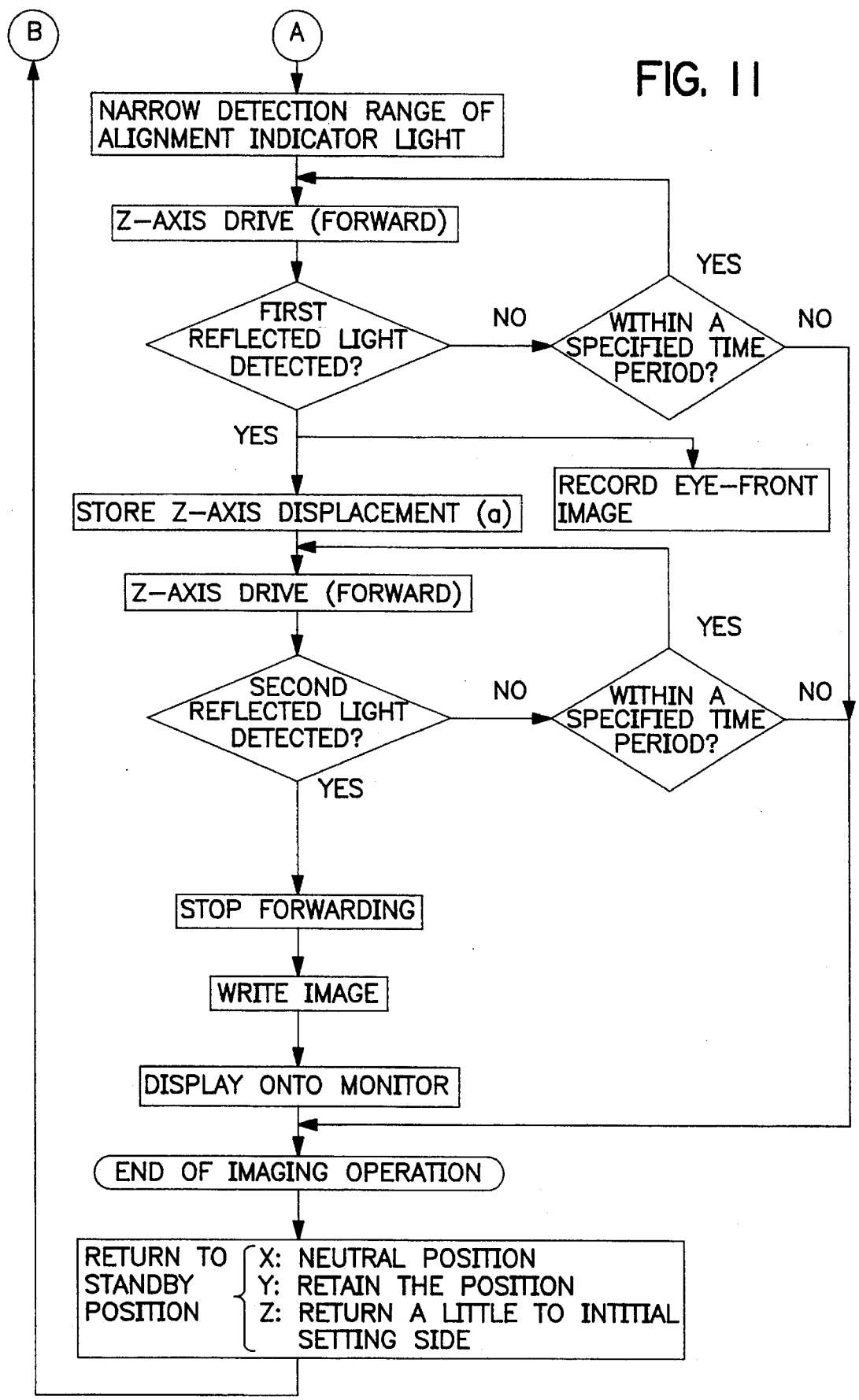
FIG. 11 is a flow chart showing the procedure subsequent to FIG. 4 in the case of cornea epithelium photographing, which is the third embodiment of the present invention.

A third embodiment of the present invention is described below, taking a case where cornea epithelium is photographed and at the same time its photographed site is displayed, by the apparatus for obtaining images of a cornea as shown in FIG. 6. First, conditions of enlarged photographing of the epithelium cells are described with reference to the optical path diagrams of cornea reflected light of the slit illuminating light of FIG. 9 and FIG. 10. Then operating procedure therefor is described based on the flow charts as shown in FIG. 4 and FIG. 11.

Figure 9:
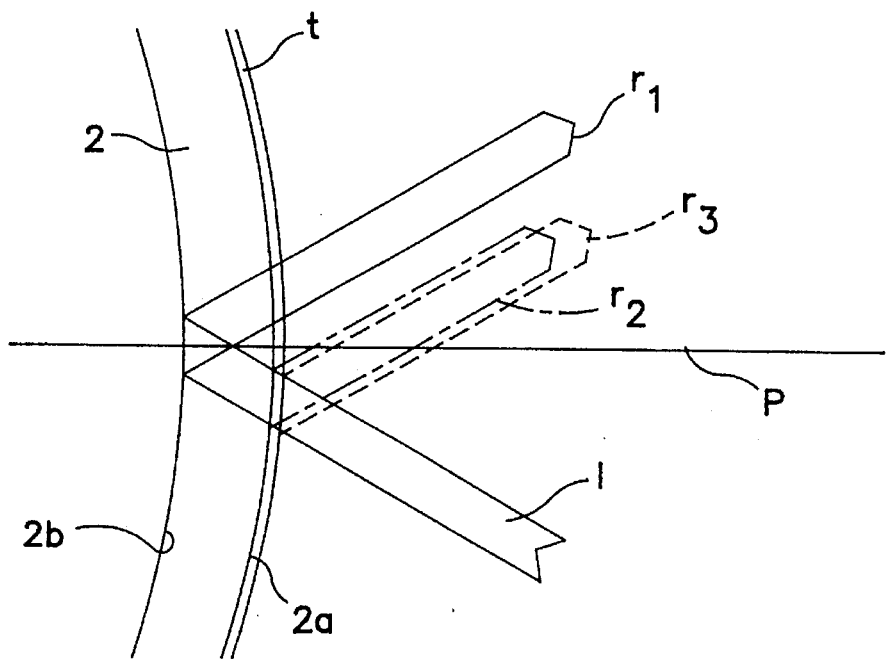
FIG. 9 is an optical path diagram of reflected light of cornea by the slit illuminating light.

FIG. 9 shows an optical path including reflected light by a lachrymal layer of the cornea surface, in the case where a cornea 2, which is the surface of a subject eye 1 to be observed, is illuminated with a slit illuminating light 1 at a specified angle obliquely with respect to a photographing direction P on the eye axis. FIG. 10 shows a similar optical path by the slit illuminating light 1 in the case where an epithelium photographing use contact lens 50 on the cornea 2.

In the case of FIG. 9, by using the thickness of the cornea 2 (approximately 0.5 mm), the slit illuminating light 1 can be separated into mirror-surface reflection from cornea endothelium 2b and reflection from cornea epithelium 2a, so that only the reflected light $r_1$ of the cornea endothelium 2b can be observed or photographed as it is enlarged. However, even if it is attempted to observe or photograph the epithelium 2a in the same manner, the presence of a thin lachrymal layer t on the cornea 2 causes its reflected light $r_3$ to overlap reflected light $r_2$, from the epithelium, so that the epithelium 2a cannot be observed or photographed.

Thus, as shown in FIG. 10, if the contact lens 50 for use of photographing epithelium is loaded on the surface of the cornea 2 so that the reflected light $r_3$ by the lachrymal layer t is separated from the reflected light $r_2$, then the reflected light $r_2$ from the epithelium can be observed or photographed as it is enlarged. Also, in this case, more specifically, a secretion layer so called a mucin layer as well as the lachrymal layer are present on the cornea epithelium 2a, making an obstacle to observation of the epithelium. The secretion layer, however, can be removed by known cleaning methods, and therefore the cleaning is exercised before the loading of the contact lens so that any effects of the layer will be eliminated. (It is noted that $r_4$ in FIG. 10 denotes surface reflection of the contact lens.)

As shown above, the present apparatus is capable of photographing the epithelium in the same way as in photographing the endothelium, by loading the epithelium-photographing use contact lens 50 onto the surface of the cornea 2.

First, the apparatus for obtaining images of a cornea is powered on, so that the optical system, which is the imaging system 3, is moved to its normal position, which is a neutral position, thus being brought into a standby state (see FIG. 4). When the subject changes and is replaced by another person, his or her ID card number is entered into the apparatus. Then, with confirmation of the movement of the optical system, i.e. the imaging system 3, to its neutral position, the head of the subject onto which the epithelium-photographing use contact lens has been loaded is fixed on the jaw plate, which is not shown. Alternatively, with the subject unchanged, when one eye of the subject is finished being photographed and the other eye is to be photographed, it is unnecessary to enter the ID card into the apparatus, in which case the head of the subject is already fixed on the jaw plate. (In this process, the head of the subject may be fixed on the jaw plate before the contact lens is loaded.)

Next, for alignment, the near-infrared LED 23 and the visible-light LED 24 are lit, and the subject is instructed to fixedly view the blinking visible light from the visible-light LED 24, which is a fixed indicator, where the start button is pressed. Then, the monitor 33 is made to present an eye-front image from the TV camera 8. Whereas the monitor 33 is displaying a light spot, which is a contact lens reflection image of the alignment-use indicator light that also serves for the position display, in the normal state, if no light spot is presented on the monitor 33, the light spot is made to come onto the monitor 33 by operating the jaw plate to adjust its height or by other operation. Automatically, or by pressing the start button when the light spot is presented on the monitor 33, the X- and Y-axes are driven to move the imaging system 3 with respect to the subject eye, depending on the position of the light spot the position of which has been detected by the X- and Y-direction position detector circuit 34, whereby the light spot is moved to the specified position (center) on the screen.

When the light spot has come to around the specified center in this way, the detection range of the alignment indicator reflected light on the monitor screen is narrowed so that noise light is prevented from mixing in the subsequent alignment (see FIG. 11). Then with alignment effected within the narrowed range, the Z-axis is driven to make the imaging system 3 move forward. During this forward movement of the imaging system 3, reflection of the slit light from the contact lens 50, which is a first reflected light, is detected by the slit-light reflection detector circuit 41. When the first reflection is detected, the infrared LEDs 45, 45 arranged sideway in front of the optical axis 4 of the eye-front observation optical system of the imaging system 3 instantaneously light so that the eye-front image in which the alignment-use light spot, which serves also as the position detection indicator, is positioned on the monitor screen, is stored in the frame memory 32, while a travel (a) in the Z-axis direction (a) is stored in the Z-direction travel detector 43.

When the reflected light from the contact lens 50, which is the first reflected light, is not detected, detection of the first reflected light is continued if the reflection detection is within a specified time period since the light spot has entered the specified position on the monitor screen. However, if no signal enters the specified position when the specified time has elapsed, there would be malfunction so that the imaging system 3 should be returned to a standby position, which will be described later, without photographing, and the procedure should be redone. In such a case, the imaging system 3 is to be returned to the initial neutral position by a signal from an unshown limit switch provided for the Z-axis motion amount.

Then, the imaging system 3 continues moving forward by Z-axis drive. Also, the slit light reflection from the cornea epithelium 2a, which is a second reflected light, is detected by the slit-light reflection detector circuit 41. When the epithelium reflection has been detected, the Z-axis drive is stopped so that the imaging system 3 is stopped from moving forward, by a signal of the epithelium reflection detection. At the same time, with strobe light emitted, photographing is done with the TV camera 8, and an image of the enlarged cornea endothelium cell image is written into the frame memory 32. The then resulting Y value (height) of the imaging system 3 is stored in the X- and Y-direction position detector circuit 34, and the photographed enlarged image of cornea epithelium cells and the eye-front image which has previously photographed and written into the memory 32 and in which the light spot 40₁ by the cornea reflected light from the contact lens 50 is positioned are displayed on the monitor 33. Thus, the photographing is completed (see FIG. 7). It is to be noted that there is no display of instruction of the operator in the data display section 48 of the screen.

On the other hand, when epithelium reflection, which is the second reflected light by the slit light, has not been detected, the epithelium reflection detection can be continued if the reflection detection is within a specified time period since the light spot has entered the specified position on the monitor screen. However, if a specified time has elapsed since then, there would be malfunction, so that the imaging system 3 should be returned to a standby state, which will be described later, and the procedure should be redone.

After photographing, the imaging system 3 is automatically returned to the standby position in the X-, Y-, and Z-directions, thus put into standby state. In this process, the movement in the X-direction of the imaging system 3, i.e. rightward and leftward with respect to the optical axis 4, is such that the imaging system 3 is returned to the neutral position, which is the operation center. The movement in the Y-direction of the imaging system 3, i.e. upward and leftward with respect to the optical axis 4, is such that the height represented by the Y value at the time when reflection of slit light from the epithelium is detected is used as it is. The movement in the Z-direction, i.e. forward and backward, is such that the imaging system 3 is moved back a little toward the initial setting position from the (a) position where the reflection of slit light from the surface of the contact lens 50, which is the first reflected light, has been detected. Thus, with the subject unchanged, the photographing can be carried out more quickly when cornea epithelium is to be photographed with the eye changed, as in the foregoing case of photographing endothelium.

It is noted that in operation of the imaging apparatus of each of the above-described embodiments, it may be before fixing the head of the subject on the jaw plate or the like that the photographing is started by pressing the start button to display an image from the TV camera onto the monitor. Also, the imaging system 3 has been so arranged in electrical fashion as to automatically move for focusing on the cornea cells of cornea endothelium or epithelium or the like of the subject eye and for measuring cornea thickness in the embodiments of the present imaging apparatus, yet it is of course also possible to manually move the imaging system 3 for focusing on the cornea cells and measuring the cornea thickness.

According to the method for obtaining images of a cornea of the present invention as will be described in claim 1, for observing or photographing an enlarged image of cornea cells of an eyeball of a subject, optical axis adjustment (alignment) can be automatically accomplished with noise light excluded with respect to the eyeball that is normally moving, while focusing can be automatically accomplished, with the use of an imaging system equipped with a TV camera. Thus, enlarged photographing of cornea cells for medical treatment can be carried out successfully and promptly by obviating the labors of manual operation involved in photographing.

According to the method for obtaining images of a cornea of the present invention as will be described in claim 2, for observing or photographing an enlarged image of cornea cells of an eyeball of a subject, optical axis alignment can be automatically accomplished while focusing can be accomplished automatically with the use of an imaging system equipped with a TV camera, whereby photograph of cornea cells for medical treatment can be carried out successfully and promptly. Moreover, when the subject is unchanged and the eye is exchanged between right and left to be photographed, the travel of the mechanics required can be reduced by utilizing positional data obtained in the preceding photographing of cornea, so that the photographing is carried out faster.

According to the method for obtaining images of a cornea as will be described in claim 3, the alignment of the subject eye and the focusing of cornea endothelium are accomplished automatically, so that enlarged photographing of cornea endothelium cells for medical treatment can be carried out successfully and promptly. Moreover, when the subject is unchanged and his or her eye is changed between right and left to be photographed, the travel of the mechanics required can be reduced so that the photographing of cornea endothelium can be carried out faster.

According to the method for obtaining images of a cornea as will be described in claim 4, the alignment of the subject eye and the focusing of cornea epithelium can be accomplished automatically, so that enlarged photographing of cornea epithelium cells for medical treatment can be carried out successfully and promptly. Moreover, when the subject is unchanged and his or her eye is exchanged between right and left to be photographed, the travel of the mechanics required can be reduced, whereby the photographing of cornea epithelium can be carried out faster.

According to the apparatus for obtaining images of a cornea of the present invention as will be described in claim 5, the focusing on cornea cells of an eyeball of a subject can be accomplished automatically in photographing enlarged images of cornea cells of cornea endothelium and epithelium and the like of the eyeball of the subject at a great magnification factor. Thus, enlarged photographing of the cornea cells can be carried out promptly by omitting the manual focusing operation in photographing, contributing to improvement in efficiency in medical treatment in ophthalmology.

According to the apparatus for obtaining images of a cornea of the present invention as will be described in claim 6, the alignment and focusing can be accomplished to photograph enlarged images of cornea cells of a subject part without requiring any skilled photographing techniques in photographing enlarged image of cornea cells of cornea endothelium and epithelium and the like of the eyeball of the subject at a great magnification factor. Moreover, together with the enlarged image of the cornea cells of the subject part, an eye-front image in which the light spot for position display projected on the eyeball surface is positioned can be recorded. Thus, it can be easily known what site of the eyeball surface the enlarged image of cornea cells such as cornea endothelium and epithelium of the subject part is, contributing to medical treatment in ophthalmology.

According to the apparatus for obtaining images of a cornea as will be described in claim 7, cornea thickness can be measured simultaneously when the photographing of cornea endothelium of the eyeball of the subject is done. Thus, additional apparatus and its operation for measurement of cornea thickness are not required, contributing to improvement in efficiency in medical treatment in ophthalmology.

According to the apparatus for obtaining images of a cornea as will be described in claim 8 or 9, an enlarged image of cornea epithelium cells, which has been considered as difficult to do, as well as an eye-front image showing the photographing site can be easily photographed by photographing with a specified contact lens loaded onto the subject eye. Moreover, the eye-front image can be recorded by an epithelium focusing detection signal and photographed as it is enlarged by an endothelium focusing detection signal, by photographing with the contact lens unloaded. Thus, an eye-front image with high positional accuracy of the light spot on the eye-front image showing the photographing site of the focused enlarged image can be recorded together with the enlarged image of cornea endothelium cells of the subject part.

What is claimed is:

1. A method for observing and photographing a cornea comprising:

automatically moving an imaging system, as a whole, which comprises an eye-front observation optical system, an illuminating system which is formed integrally with the observation optical system and which illuminates through a slit an eyeball surface in a direction different from that in which the observation optical system does, and enlarged-imaging optical system capable of observing or photographing a subject part as it is enlarged by a TV camera based on the slit illuminating light with which the eyeball surface has been illuminated, depending on a position on a monitor screen of reflected light obtained by picking up by a TV camera cornea reflected light of alignment-use indicator light projected toward a subject eye coaxially with the optical axis of the eye-front observation optical system, in a direction perpendicular to the optical axis of the observation optical system, so that a light spot on the monitor screen by the reflected light is brought to a specified position on the screen;

driving the whole imaging system start to move forward in the direction toward the subject eye while continuing the movement in the direction perpendicular to the optical axis so that said light spot tracks the specified position on the screen, with a detection range of the light spot narrowed so as to eliminate detections of noises other than the light spot, when the light spot has come to around a specified area on the screen, and detecting focusing of the enlarged-imaging optical system on the cornea subject part by a photo-detector having a light-receiving surface at such a position on the optical axis of the enlarged-imaging optical system that its optical path is other than that of the TV camera, whereby an enlarged image of cornea cells of the subject part is photographed.

2. A method for observing and photographing a cornea, comprising:

automatically moving an imaging system, as a whole, which comprises an eye-front observation optical system, an illuminating system which is formed integrally with the observation optical system and which illuminates through a slit an eyeball surface in a direction different from that in which the observation optical system does, and an enlarged-imaging optical system capable of observing or photographing a subject part as it is enlarged by a TV camera based on the slit illuminating light with which the eyeball surface has been illuminated, depending on a position on a monitor screen of reflected light obtained by picking up by a TV camera cornea reflected light of alignment-use indicator light projected toward a subject eye coaxially with the optical axis of the eye-front observation optical system, in a direction perpendicular to the optical axis of the observation optical system, so that a light spot on the monitor screen by the reflected light is brought to a specified position of the screen;

driving the whole imaging system start to move forward so as to track the light spot in the direction toward the subject eye, when the light spot has come to around a specified area on the screen;

detecting focusing of the enlarged-imaging optical system on the cornea subject part by a photo-detector having a light-receiving surface at such a position on the optical axis of the enlarged-imaging optical system that its optical path is other than that of the TV camera, whereby an enlarged image of cornea cells of the subject part is photographed;

after the imaging system has photographed an enlarged image of cornea cells of the subject part, canceling a travel of the observation optical system in an X-direction while retaining a travel thereof in a Y-direction, out of travels in directions perpendicular to the optical axis of the observation optical system, whereby the imaging system is automatically returned to its initial setting side by a specified small distance from the cornea cell focusing detection position.

3. The method for observing and photographing a cornea according to claim 1 or 2, wherein said subject part is a cornea endothelium.

4. The method for observing and photographing a cornea according to claim 1 or 2, wherein said subject part is a cornea epithelium.

5. An apparatus for observing and photographing a cornea, comprising at least:

an illuminating system for illuminating through a slit an eyeball surface of a subject eye;

an enlarged-imaging optical system for forming an enlarged image of a subject part of the subject eye based on slit illuminating light with which the eyeball surface has been illuminated;

means for emitting an indicator light toward the eye so that the indicator light is reflected back at the cornea of the eye;

a video camera provided in front of the subject eye and having a light receiving surface for receiving the enlarged image of the subject eye and receiving the indicator light reflected at the cornea surface;

a focusing-detection use photo-detector arranged so as to detect a focusing of the enlarged image of the subject part of the light receiving surface of the video camera and positioned via an optical path other than that via which the enlarged image has been formed by the enlarged-imaging optical system;

detection-means for detecting the indicator light received by the light receiving surface of the video camera;

means for narrowing a detection range of the indicator light by said detection means so as to eliminate detections of noises other than the indicator light;

means for moving an imaging system, as a whole, having the illuminating system, the enlarged-imaging optical system, the means for emitting an indicator light, the video camera and the focusing-detection use photo-detector by signals from the video camera and the focusing-detection use photo-detector so that the imaging system is brought to the focusing position of the subject part; and means for generating a signal for photographing the enlarged image of the subject part of the eye based on a signal of having detected the focusing of the subject part by the focusing-detection use photo-detector.

6. An apparatus for observing and photographing a cornea, comprising:

a position-detection indicator projecting means arranged opposite to a subject eye for indicating a subject part of the eye when photographed by emitting an indicator light toward the eye so that the indicator light is reflected back at a cornea surface of the eye;

an eye-front observation means equipped with a video camera in front of the eye having a light receiving surface for receiving the indicator light reflected at the cornea surface;

an illuminating system for illuminating through a slit an eyeball surface of the subject eye;

an enlarged-observation means equipped with an enlarged-imaging optical system for forming and observing an enlarged image of the subject part based on slit illuminating light with which the eyeball surface has been illuminated;

a subject-part focusing detection means having a focusing-detection use photo-detector and arranged so as to detect-focusing of the enlarged image of the subject part formed by the enlarged-imaging optical system on the light receiving surface of the video camera;

detection-means for detecting the indicator light received by the light receiving surface of the video camera;

means for narrowing a detection range of the indicator light by said detection-means so as to eliminate detections of noises other than the indicator light;

means for moving an imaging system, as a whole, having the position-detection indicator projecting means, the eye-front observation means, the illuminating system, the enlarged-imaging optical system, and the focusing-detection use photo-detector in both a direction perpendicular to an optical axis of the eye-front observation means with respect to the subject eye and a direction toward the subject eye; and means for recording both an eye-front image in the eye-front observation means and the enlarged image of the subject part in the enlarged observation means, wherein alter reflected light from the subject part of the position detection indicator is brought to a specified position in the eye-front image formed by the eye-front observation means, the eye-front image is recorded and the enlarged image of the subject part is recorded by a focusing-detection signal from the subject-part focusing detection means.

7. The apparatus for observing and photographing a cornea according to claim 5 or 6, wherein said focusing-detection use photo-detector is a photo-detector so arranged as to detect a cornea epithelium focusing position and a cornea endothelium focusing position by said enlarged-imaging optical system, said apparatus for obtaining images of a cornea further comprising means for detecting a travel of said imaging system from the cornea epithelium focusing position to the cornea endothelium focusing position, both positions having been detected by said focusing-detection use photo-detector, whereby cornea thickness can be measured while the cornea endothelium can be photographed.

8. The apparatus for observing and photographing a cornea according to claim 6, wherein an eye-front image is recorded by a first focusing detection signal from said focusing detection means of the subject part, and an enlarged image of the cornea cells of the subject part is recorded by a second focusing detection signal.

9. The apparatus for observing and photographing a cornea according to claim 6, wherein an eye-front image is recorded by a cornea epithelium focusing detection signal from said focusing detection means of the subject part, and an enlarged image of the cornea endothelium cells of the subject part is recorded by a cornea endothelium focusing detection signal.

10. A method for observing and photographing a cornea by automatically moving an optical unit, as a whole, having:

first optical means for observing a frontal portion of an eye via a video camera provided in front of the eye;

second optical means for illuminating and for flashing an eyeball surface through a slit in a direction different from that of a first optical axis of the first optical means;

third optical means for emitting an indicator light toward the eyeball along the first optical axis so that the indicator light is reflected back at a cornea surface of the eye along the first optical axis and reaches a light receiving surface of the video camera;

fourth optical means for observing and photographing an enlarged visual image of a subject portion of the cornea via the video camera based of an illumination and a flash light of the second optical means reflected at the cornea surface; and a receiving optics having a light receiving surface, which provided along a fifth optical axis separated from a fourth optical axis of the fourth optical means, for detecting a focusing of the enlarged visual image of the subject portion of the cornea at the light receiving surface of the video camera, which comprises the steps of displaying the indicator light as a light spot on a screen of a video monitor;

shifting the optical unit in a transverse direction with respect to the first optical axis in response to a location of the light spot on the monitor screen so that the light spot on the monitor screen is shifted to a specified location on the screen;

narrowing a detection range of the light spot on the screen when the light spot has entered within a specified range on the screen so as to eliminate detections of noises other than the light spot;

advancing the optical unit in a direction toward the eye while continuing the shifting of the unit in the transverse direction in response to the location of the light spot on the screen so that the light spot chases the specified location on the screen; and photographing the enlarged visual image of the subject portion of the cornea via the video camera when the receiving optics detects the focusing.

11. A method for observing and photographing a cornea by automatically moving an optical unit, as a whole, having:

first optical means for observing a frontal portion of an eye via a video camera provided in front of the eye;

second optical means for illuminating and for flashing an eyeball surface through a slit in a direction different from that of a first optical axis of the first optical means;

third optical means for emitting an indicator light toward the eyeball along the first optical axis so that the indicator light is reflected back at a cornea surface of the eye along the first optical axis and reaches a light receiving surface of the video camera;

fourth optical means for obtaining an enlarged visual image of a subject portion of the cornea via the video camera based of a flash light of the second optical means reflected at the cornea surface; and a receiving optics having a light receiving surface, which provided along a fifth optical axis separated from a fourth optical axis of the fourth optical means, for detecting a focusing of the enlarged visual image of the subject portion of the cornea at the light receiving surface of the video camera, which comprises the steps of displaying the indicator light as a light spot on a screen of a video monitor;

shifting the optical unit in a transverse direction with respect to the first optical axis in response to a location of the light spot on the monitor screen so that the light spot on the monitor screen is shifted to a specified location on the screen;

advancing the optical unit in a direction toward the eye when the light spot has entered within a specified range on the screen while continuing the shifting of the unit in the transverse direction in response to the location of the light spot on the screen so that the light spot chases the specified location on the screen;

photographing the enlarged visual image of the subject portion of the cornea via the video camera when the receiving optics detects the focusing; and moving the optical unit to a neutral position with respect to a left and right direction of the eye and receding the unit by a specified small distance toward the video camera from a focus detecting position while maintaining a vertical position of the unit.

12. The method for observing and photographing a cornea according to claim 10 or 11, wherein said subject portion is a cornea endothelium.

13. The method for observing and photographing a cornea according to claim 10 or 11, wherein said subject portion is a cornea epithelium.

14. The method for observing and photographing a cornea according to claim 10 or 11, wherein said third optical means comprises a target lamp for emitting a visible light toward the eyeball along the first optical axis so that a patient looks at the visible light from the target lamp, thereby fixing the eye with respect to the first optical axis.

15. An apparatus for observing and photographing a cornea by automatically moving an optical unit, as a whole, having:

first optical means for observing a frontal portion of an eye via a video camera provided in front of the eye;

second optical means for illuminating and for flashing an eyeball surface through a slit in a direction different from that of a first optical axis of the first optical means;

third optical means for emitting an indicator light toward the eyeball along the first optical axis so that the indicator light is reflected back at a cornea surface of the eye along the first optical axis and reaches a light receiving surface of the video camera;

fourth optical means for observing and photographing an enlarged visual image of a subject portion of the cornea via the video camera based of an illumination and a flash light of the second optical means reflected at the cornea surface; and a receiving optics having a light receiving surface, which provided along a fifth optical axis separated from a fourth optical axis of the fourth optical means, for detecting a focusing of the enlarged visual image of the subject portion of the cornea at the light receiving surface of the video camera, said apparatus further comprising:

a video monitor for displaying the indicator light as a light spot on a screen;

means for shifting the optical unit in a transverse direction with respect to the first optical axis in response to a location of the light spot on the monitor screen so that the light spot on the monitor screen is shifted to a specified location on the screen;

switching means for narrowing a detection range of the light spot on the screen when the light spot has entered within a specified range on the screen so as to eliminate detections of noises other than the light spot;

means for advancing the optical unit toward the eye until said receiving optics detects the focusing; and means for photographing the enlarged visual image of the subject portion of the cornea via the video camera when the receiving optics detects the focusing.

16. An apparatus for observing and photographing a cornea by automatically moving an optical unit, as a whole, having:

first optical means for observing a frontal portion of an eye via a video camera provided in front of the eye;

second optical means for illuminating and for flashing an eyeball surface through a slit in a direction different from that of a first optical axis of the first optical means;

third optical means for emitting an indicator light toward the eyeball along the first optical axis so that the indicator light is reflected back at a cornea surface of the eye along the first optical axis and reaches a light receiving surface of the video camera;

fourth optical means for observing and photographing an enlarged visual image of a subject portion of the cornea via the video camera based of an illumination and a flash light of the second optical means reflected at the cornea surface; and a receiving optics having a light receiving surface, which provided along a fifth optical axis separated from a fourth optical axis of the fourth optical means, for detecting a focusing of the enlarged visual image of the subject portion of the cornea at the light receiving surface of the video camera, said apparatus further comprising:

a video monitor for displaying the indicator light as a light spot on a screen;

switching means for narrowing a detection range of the light spot on the screen when the light spot has entered within a specified range on the screen so as to eliminate detections of noises other than the light spot;

shifting and advancing means for shining the optical unit in a transverse direction with respect to the first optical axis in response to a location of the light spot on the monitor screen and for advancing the optical unit in a direction toward the eye while continuing the shifting of the unit in the transverse direction in response to the location of the light spot on the screen so that the light spot chases a specified location on the screen; and image storing means for storing visual images obtained by the first and fourth optical means, wherein an image of the frontal portion of the eye is stored when the light spot has aligned with the specified location and the enlarged image when the receiving optics detects the focusing.

17. An apparatus for observing and photographing a cornea according to claim 15 or 16, wherein:

said receiving optics detects the focusing of a cornea epithelium and the focusing of a cornea endothelium; and said apparatus further comprises displacement measuring means of the optical unit in the advancing direction, thereby a thickness of the cornea can be measured.

18. An apparatus for observing and photographing a cornea according to claim 16, wherein:

said storing means stores an image of the frontal portion of the eye when the focus detecting means detects the focusing of a cornea epithelium and the enlarged visual image of the subject portion of the cornea when the focus detecting means detects the focusing of a cornea endothelium.

19. The apparatus for observing and photographing a cornea according to claim 15 or 16, wherein said third optical means comprises a target lamp for emitting a visible light toward the eyeball along the first optical axis so that a patient looks at the visible light from the target lamp, thereby fixing the eye with respect to the first optical axis.

* * * * *

UNITED STATES PATENT AND TRADEMARK OFFICE
CERTIFICATE OF CORRECTION

PATENT NO. : 5,548,354
DATED : August 20, 1996
INVENTOR(S) : Tatsuya Kasahara, et al.

It is certified that error appears in the above-identified patent and that said Letters Patent is hereby corrected as shown below:

On title page,

Item [75] Inventors: Change "Tatsuya Kasahara; Hamada Yoichi, both of Nishinomiya, Japan" to --TATSUYA KASAHARA; YOICHI HAMADA, BOTH OF NISHINOMIYA, JAPAN--

Signed and Sealed this

Twelfth Day of November, 1996

Attest:

BRUCE LEHMAN

*Attesting Officer*    *Commissioner of Patents and Trademarks*